(12) United States Patent
Kato et al.

(10) Patent No.: US 12,300,019 B2
(45) Date of Patent: *May 13, 2025

(54) DETECTION DEVICE

(71) Applicants: Japan Display Inc., Tokyo (JP); The University of Tokyo, Tokyo (JP)

(72) Inventors: Hirofumi Kato, Tokyo (JP); Makoto Uchida, Tokyo (JP); Takanori Tsunashima, Tokyo (JP); Takashi Nakamura, Tokyo (JP); Akio Takimoto, Tokyo (JP); Takao Someya, Tokyo (JP); Tomoyuki Yokota, Tokyo (JP)

(73) Assignees: Japan Display Inc., Tokyo (JP); The University of Tokyo, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/501,351

(22) Filed: Nov. 3, 2023

(65) Prior Publication Data

US 2024/0071128 A1 Feb. 29, 2024

Related U.S. Application Data

(63) Continuation of application No. 17/500,147, filed on Oct. 13, 2021, now Pat. No. 11,854,299, which is a (Continued)

(30) Foreign Application Priority Data

Apr. 17, 2019 (JP) ................................ 2019-078924

(51) Int. Cl.
*G06V 40/13* (2022.01)
*A61B 5/1172* (2016.01)
(Continued)

(52) U.S. Cl.
CPC ........ *G06V 40/1324* (2022.01); *A61B 5/1172* (2013.01); *G06F 21/32* (2013.01);
(Continued)

(58) Field of Classification Search
CPC ............... G06V 40/1324; G06V 40/13; G06V 40/1341; G06V 40/1365; G06V 40/145;
(Continued)

(56) References Cited

U.S. PATENT DOCUMENTS 10,852,122 B2  12/2020 Kern et al.
11,854,299 B2 * 12/2023 Kato .................... A61B 5/1172
(Continued)

FOREIGN PATENT DOCUMENTS

JP   H07299043 A   11/1995
JP   2009026220 A   2/2009
(Continued)

OTHER PUBLICATIONS

Office Action issued in related Chinese Patent Application No. 202080028835.1 on Dec. 12, 2023 and English translation of same. 18 pages.
(Continued)

*Primary Examiner* — John B Strege
(74) *Attorney, Agent, or Firm* — K&L Gates LLP

(57) ABSTRACT

A detection device includes a plurality of optical sensors arranged in a detection area, a light source configured to emit light that is emitted to an object to be detected and is detected by the optical sensors, and a processor configured to perform processing based on outputs from the optical sensors. The processor is configured to determine, based on the outputs of the respective optical sensors obtained at a cycle of a predetermined period, an optical sensor an output of which is to be employed from among the optical sensors.

10 Claims, 27 Drawing Sheets

Related U.S. Application Data continuation of application No. PCT/JP2020/016502, filed on Apr. 15, 2020.

(51) Int. Cl.
  *G06F 21/32* (2013.01)
  *G06V 40/12* (2022.01)
  *G06V 40/145* (2022.01)

(52) U.S. Cl.
  CPC .......... *G06V 40/13* (2022.01); *G06V 40/1341* (2022.01); *G06V 40/1365* (2022.01); *G06V 40/145* (2022.01)

(58) Field of Classification Search
  CPC . G06V 40/1318; A61B 5/1172; A61B 5/1171; G06F 21/32; G06T 1/00
  See application file for complete search history.

(56) References Cited

U.S. PATENT DOCUMENTS

| | | |
|---|---|---|
| 2009/0027358 A1 | 1/2009 | Hosono |
| 2011/0112379 A1 | 5/2011 | Li et al. |
| 2012/0150047 A1 | 6/2012 | Terumoto et al. |
| 2013/0261415 A1* | 10/2013 | Ashe ................. A61B 5/14552 600/323 |
| 2014/0253787 A1 | 9/2014 | Shu et al. |
| 2017/0319084 A1 | 11/2017 | Fujiwara |
| 2018/0060642 A1 | 3/2018 | Kim et al. |
| 2019/0156095 A1* | 5/2019 | Moon ................. G06V 40/1359 |
| 2020/0285722 A1 | 9/2020 | He et al. |
| 2020/0327302 A1 | 10/2020 | He et al. |

FOREIGN PATENT DOCUMENTS

| | | |
|---|---|---|
| JP | 2009032005 A | 2/2009 |
| JP | 2012120772 A | 6/2012 |
| JP | 2012147925 A | 8/2012 |
| JP | 2016096848 A | 5/2016 |
| JP | 2016122072 A | 7/2016 |
| WO | 2012005163 A1 | 1/2012 |

OTHER PUBLICATIONS

Office Action issued in related Chinese Patent Application No. 202080028835.1 on May 30, 2024 and English translation of same. 17 pages.

International Search Report issued in International Patent Application No. PCT/JP2020/016502 on Jun. 16, 2020 and English translation of same. 6 pages.

International Written Opinion issued in International Patent Application No. PCT/JP2020/016502 on Jun. 16, 2020. 4 pages.

Office Action issued in related Japanese Patent Application No. 2021-514181 on Nov. 1, 2022 and English translation of same. 6 pages.

* cited by examiner

DETECTION DEVICE

CROSS-REFERENCE TO RELATED APPLICATION

This application is a continuation application of U.S. patent application Ser. No. 17/500,147, filed on Oct. 13, 2021, which is a continuation of International Patent Application No. PCT/JP2020/016502 filed on Apr. 15, 2020, which claims the benefit of priority from Japanese Patent Application No. 2019-078924 filed on Apr. 17, 2019, the entire contents of which are incorporated herein by reference.

BACKGROUND

Technical Field

What is disclosed herein relates to a detection device.

Description of the Related Art

Optical sensors capable of detecting a fingerprint pattern and/or a vascular pattern are known (for example, Japanese Patent Application Laid-open Publication No. 2009-032005).

When the optical sensor is brought into proximity to or contact with an object to be detected in order to detect the fingerprint pattern or the vascular pattern, a variation such as a positional shift may occur in the positional relation between the optical sensor and the object to be detected due to activities of a living body.

For the foregoing reasons there is a need for a detection device capable of responding to a change in positional relation between an optical sensor and an object to be detected.

SUMMARY

According to an aspect, a detection device includes: a plurality of optical sensors arranged in a detection area; a light source configured to emit light that is emitted to an object to be detected and is detected by the optical sensors; and a processor configured to perform processing based on outputs from the optical sensors. The processor is configured to determine, based on the outputs of the respective optical sensors obtained at a cycle of a predetermined period, an optical sensor an output of which is to be employed from among the optical sensors.

DETAILED DESCRIPTION

Figure 1:
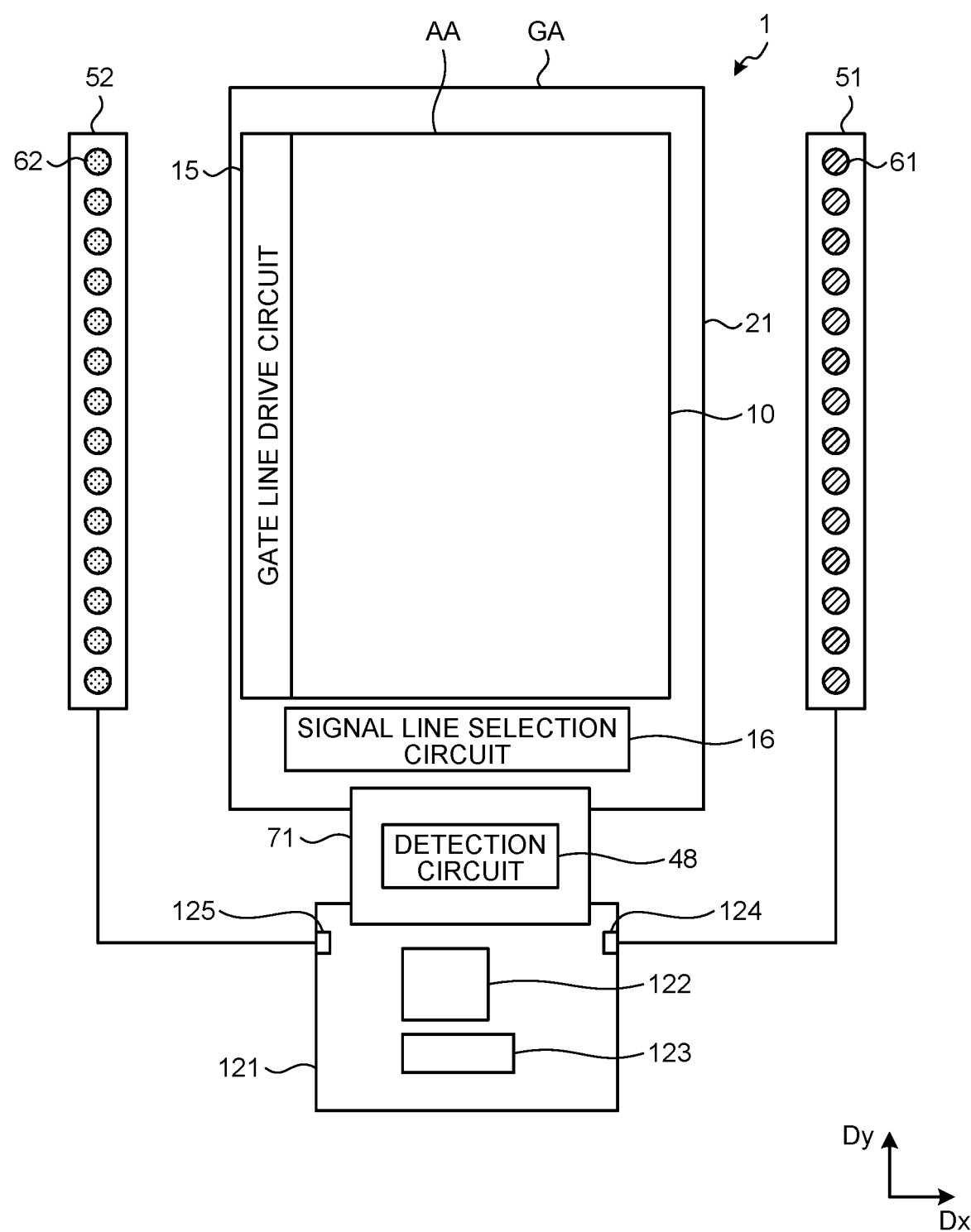
FIG. 1 is a plan view illustrating a detection device according to a first embodiment.

The following describes modes (embodiments) for carrying out the present invention in detail with reference to the drawings. The present invention is not limited to the description of the embodiments given below. Components described below include those easily conceivable by those skilled in the art or those substantially identical thereto. Moreover, the components described below can be appropriately combined. The disclosure is merely an example, and the present invention naturally encompasses appropriate modifications easily conceivable by those skilled in the art while maintaining the gist of the invention. To further clarify the description, the drawings schematically illustrate, for example, widths, thicknesses, and shapes of various parts as compared with actual aspects thereof, in some cases. However, they are merely examples, and interpretation of the present invention is not limited thereto. The same element as that illustrated in a drawing that has already been discussed is denoted by the same reference numeral through the description and the drawings, and detailed description thereof will not be repeated in some cases where appropriate.

In this disclosure, when an element is described as being "on" another element, the element can be directly on the other element, or there can be one or more elements between the element and the other element.

First Embodiment

FIG. 1 is a plan view illustrating a detection device according to a first embodiment. As illustrated in FIG. 1, a detection device 1 includes a sensor base member 21, a sensor 10, a gate line drive circuit 15, a signal line selection circuit 16, a detection circuit 48, a control circuit 122, a power supply circuit 123, a first light source base member 51, a second light source base member 52, at least one first light source 61, and at least one second light source 62.

A control board 121 is electrically coupled to the sensor base member 21 through a flexible printed circuit board 71. The flexible printed circuit board 71 is provided with the detection circuit 48. The control board 121 is provided with the control circuit 122 and the power supply circuit 123. The control circuit 122 is, for example, a field programmable gate array (FPGA). The control circuit 122 supplies control signals to the sensor 10, the gate line drive circuit 15, and the signal line selection circuit 16 to control a detection operation of the sensor 10. The control circuit 122 supplies control signals to the first light sources 61 and the second light sources 62 to control to turn on and off the first light sources 61 and the second light sources 62. The power supply circuit 123 supplies voltage signals including, for example, a sensor power supply signal VDDSNS (refer to FIG. 4) to the sensor 10, the gate line drive circuit 15, and the signal line selection circuit 16. The power supply circuit 123 also supplies a power supply voltage to the first light sources 61 and the second light sources 62.

The sensor base member 21 has a detection area AA and a peripheral area GA. The detection area AA is an area provided with a plurality of photodiodes PD (refer to FIG. 4) included in the sensor 10. The peripheral area GA is an area between the outer circumference of the detection area AA and ends of the sensor base member 21 and is an area not overlapping the photodiodes PD.

The gate line drive circuit 15 and the signal line selection circuit 16 are provided in the peripheral area GA. Specifically, the gate line drive circuit 15 is provided in an area of the peripheral area GA extending along a second direction Dy, and the signal line selection circuit 16 is provided in an area of the peripheral area GA extending along a first direction Dx and is provided between the sensor 10 and the detection circuit 48.

The first direction Dx is a direction in a plane parallel to the sensor base member 21. The second direction Dy is a direction in a plane parallel to the sensor base member 21 and is a direction orthogonal to the first direction Dx. The second direction Dy may intersect the first direction Dx without being orthogonal thereto. A third direction Dz is a direction orthogonal to the first direction Dx and the second direction Dy, and is the normal direction of the sensor base member 21.

The first light sources 61 are provided on the first light source base member 51 and are arranged along the second direction Dy. The second light sources 62 are provided on the second light source base member 52, and are arranged along the second direction Dy. The first light source base member 51 and the second light source base member 52 are electrically coupled through terminals 124 and 125, respectively, provided on the control board 121 to the control circuit 122 and the power supply circuit 123.

For example, inorganic light-emitting diodes (LEDs) or organic electroluminescent (EL) diodes (organic light-emitting diodes) (OLEDs) are used as the first light sources 61 and the second light sources 62. The first light sources 61 and the second light sources 62 emit first light L61 and second light L62 (refer to, for example, FIG. 11), respectively, having wavelengths different from each other. The first light L61 and the second light L62 have different maximum emission wavelengths from each other. The term "maximum emission wavelength" refers to a wavelength that exhibits the maximum emission intensity in an emission spectrum representing a relation between the wavelength and the emission intensity of each of the first light L61 and the second light L62. Hereinafter, when a value of the wavelength is simply mentioned, the mentioned value refers to an assumed maximum emission wavelength.

The first light L61 emitted from the first light sources 61 is mainly reflected on a surface of a detection target object, for example, a finger Fg, and enters the sensor 10. Thus, the sensor 10 can detect a fingerprint by detecting a shape of asperities of the surface of, for example, the finger Fg. The second light L62 emitted from the second light sources 62 is mainly reflected inside, for example, the finger Fg, or transmitted through, for example, the finger Fg, and enters the sensor 10. Thus, the sensor 10 can detect biological information on the inside, for example, the finger Fg. The biological information is, for example, a pulse wave, pulsation, and a blood vessel image of the finger Fg or a palm.

As an example, the first light L61 may have a wavelength in a range from 520 nm to 600 nm, for example, at approximately 560 nm, and the second light L62 may have a wavelength in a range from 780 nm to 900 nm, for example, at approximately 850 nm. In this case, the first light L61 is blue or green visible light, and the second light L62 is infrared light. The sensor 10 can detect a fingerprint based on the first light L61 emitted from the first light sources 61. The second light L62 emitted from the second light sources 62 is reflected in the detection target object such as the finger Fg, or transmitted through or absorbed by, for example, the finger Fg, and enters the sensor 10. Thus, the sensor 10 can detect the pulse wave and the blood vessel image (vascular pattern) as the biological information on the inside, for example, the finger Fg.

Alternatively, the first light L61 may have a wavelength in a range from 600 nm to 700 nm, for example, at approximately 660 nm, and the second light L62 may have a wavelength in a range from 780 nm to 900 nm, for example, at approximately 850 nm. In this case, the sensor 10 can detect a blood oxygen saturation level in addition to the pulsation and the blood vessel image as the biological information based on the first light L61 emitted from the first light sources 61 and the second light L62 emitted from the second light sources 62. In this manner, since the detection device 1 includes the first light sources 61 and the second light sources 62, the detection device 1 can detect the various types of the biological information by performing the detection based on the first light L61 and the detection based on the second light L62.

The arrangement of the first light sources 61 and the second light sources 62 illustrated in FIG. 1 is merely an example, and can be changed as appropriate. For example, the first light sources 61 and the second light sources 62 may be arranged on each of the first light source base member 51 and the second light source base member 52. In this case, a group including the first light sources 61 and a group including the second light sources 62 may be arranged in the second direction Dy, or the first light source 61 and the second light source 62 may be alternately arranged in the second direction Dy. The number of the light source base members provided with the first light sources 61 and the second light sources 62 may be one, or three or more.

Figure 2:
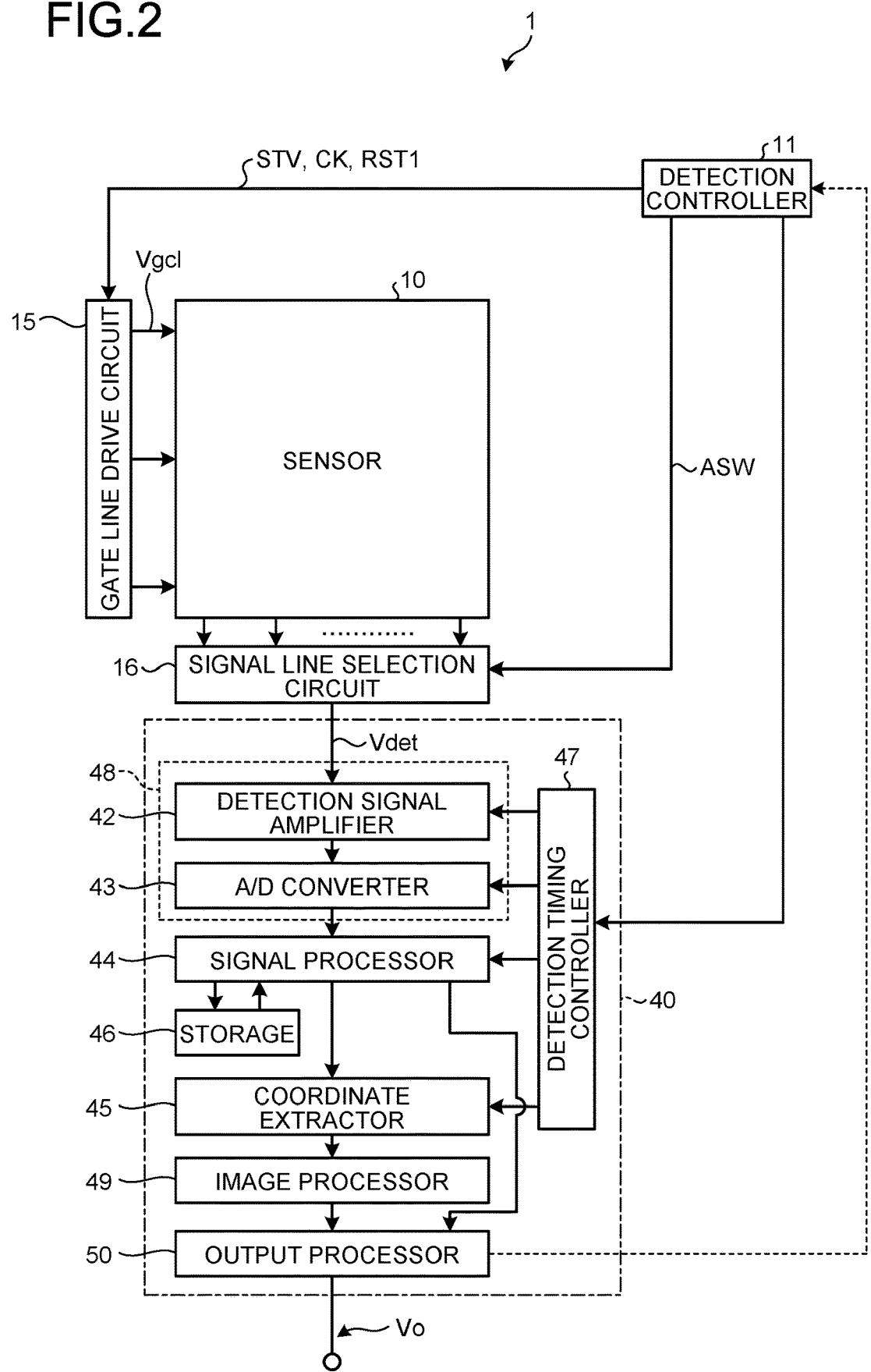
FIG. 2 is a block diagram illustrating a configuration example of the detection device according to the first embodiment.

FIG. 2 is a block diagram illustrating a configuration example of the detection device according to the first embodiment. As illustrated in FIG. 2, the detection device 1 further includes a detection controller 11 and a detector 40. The control circuit 122 includes some or all functions of the detection controller 11. The control circuit 122 also includes some or all functions of the detector 40 except those of the detection circuit 48.

The sensor 10 is an optical sensor including the photodiodes PD serving as photoelectric conversion elements. Each of the photodiodes PD included in the sensor 10 outputs an electrical signal corresponding to light emitted thereto to the signal line selection circuit 16. The signal line selection circuit 16 sequentially selects a signal line SGL in response to a selection signal ASW from the detection controller 11. As a result, the electrical signal is output as a detection signal Vdet to the detector 40. The sensor 10 performs the detection in response to a gate drive signal Vgcl supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals including, for example, a start signal STV, a clock signal CK, and a reset signal RST1 to the gate line drive circuit 15. The detection controller 11 also supplies various control signals including, for example, the selection signal ASW to the signal line selection circuit 16. The detection controller 11 also supplies various control signals to the first light sources 61 and the second light sources 62 to control to turn on and off the first light sources 61 and the second light sources 62.

The gate line drive circuit 15 is a circuit that drives a plurality of gate lines GCL (refer to FIG. 3) based on the various control signals. The gate line drive circuit 15 sequentially or simultaneously selects the gate lines GCL and supplies the gate drive signals Vgcl to the selected gate lines GCL. Through this operation, the gate line drive circuit 15 selects the photodiodes PD coupled to the gate lines GCL.

Figure 3:
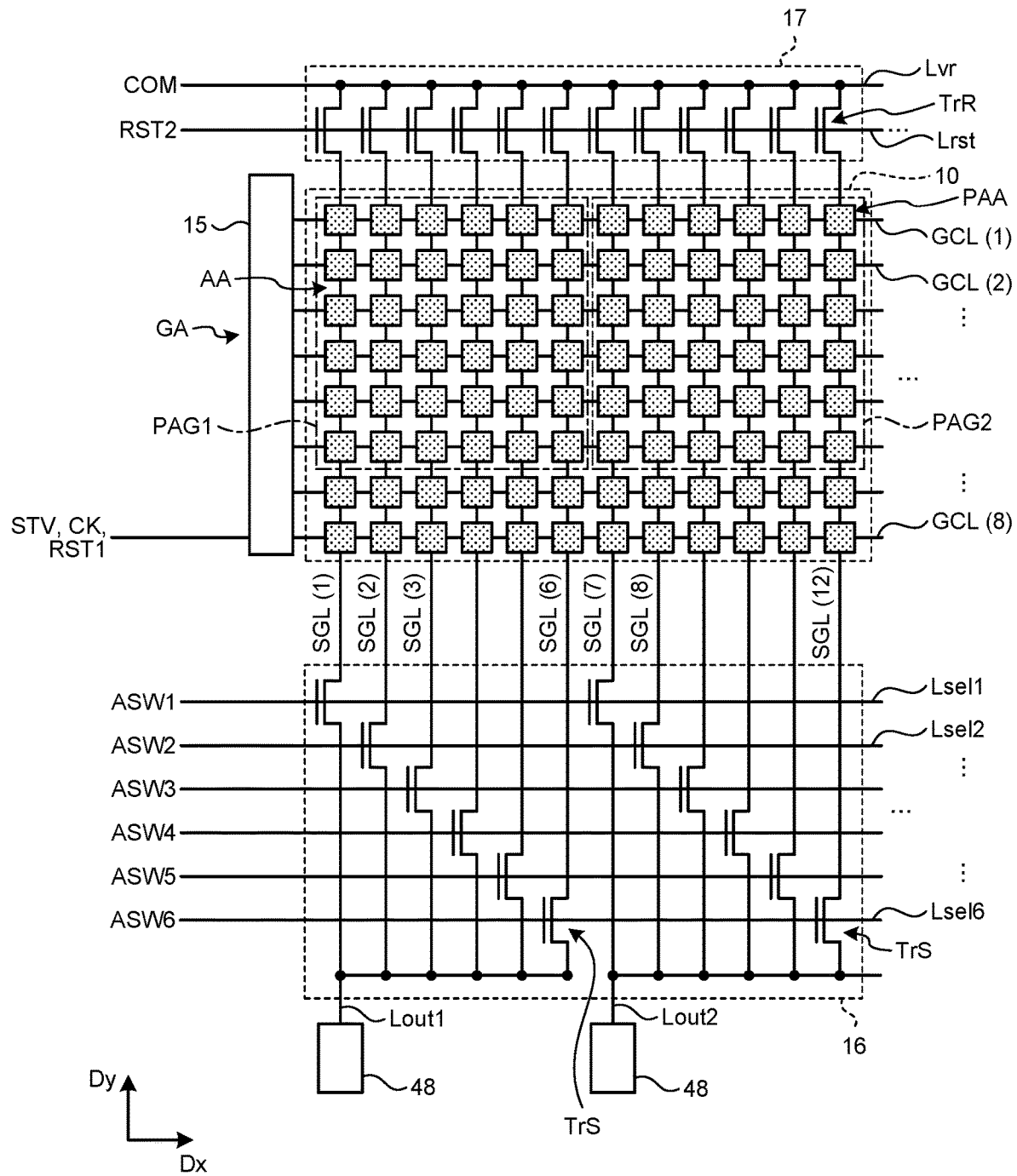
FIG. 3 is a circuit diagram illustrating the detection device.

The signal line selection circuit 16 is a switch circuit that sequentially or simultaneously selects a plurality of signal lines SGL (refer to FIG. 3). The signal line selection circuit 16 is, for example, a multiplexer. The signal line selection circuit 16 couples the selected signal lines SGL to the detection circuit 48 based on the selection signal ASW supplied from the detection controller 11. Through this operation, the signal line selection circuit 16 outputs the detection signal Vdet of each of the photodiodes PD to the detector 40.

The detector 40 includes the detection circuit 48, a signal processor 44, a coordinate extractor 45, a storage 46, a detection timing controller 47, an image processor 49, and an output processor 50. Based on a control signal supplied from the detection controller 11, the detection timing controller 47 controls the detection circuit 48, the signal processor 44, the coordinate extractor 45, and the image processor 49 so as to operate in synchronization with one another.

The detection circuit 48 is, for example, an analog front end (AFE) circuit. The detection circuit 48 is, for example, a signal processing circuit having functions of a detection signal amplifier 42 and an analog-to digital (A/D) converter 43. The detection signal amplifier 42 amplifies the detection signal Vdet. The A/D converter 43 converts an analog signal output from the detection signal amplifier 42 into a digital signal.

The signal processor 44 is a logic circuit that detects a predetermined physical quantity received by the sensor 10 based on an output signal of the detection circuit 48. When the finger Fg is in contact with or in proximity to the detection area AA, the signal processor 44 can detect the asperities on the surface of the finger Fg or the palm based on the signal from the detection circuit 48. The signal processor 44 can also detect the biological information based on the signal from the detection circuit 48. The biological information is, for example, the blood vessel image, a pulse wave, the pulsation, and/or the blood oxygen saturation level of the finger Fg or the palm.

In the case of obtaining the human blood oxygen saturation level, for example, 660 nm (the range is from 500 nm to 700 nm) is employed as the first light L61, and approximately 850 nm (the range is from 800 nm to 930 nm) is employed as the second light L62. Since the amount of light absorption changes with an amount of oxygen taken up by hemoglobin, the photodiode PD detects an amount of light obtained by subtracting the amount of light absorbed by the blood (hemoglobin) from that of each of the first light L61 and the second light L62 that have been emitted. Most of the oxygen in the blood is reversibly bound to hemoglobin in red blood cells, and a small portion of the oxygen is dissolved in blood plasma. More specifically, the value of percentage of oxygen with respect to an allowable amount thereof in the blood as a whole is called the oxygen saturation level ($SpO_2$). The blood oxygen saturation level can be calculated from the amount of light obtained by subtracting the amount of light absorbed by the blood (hemoglobin) from that of the light emitted at the two wavelengths of the first light L61 and the second light L62.

The signal processor 44 may acquire the detection signals Vdet (biological information) simultaneously detected by the photodiodes PD, and average the detection signals Vdet. In this case, the detector 40 can perform the stable detection by reducing a measurement error caused by noise or a relative displacement between the detection target object such as the finger Fg and the sensor 10.

The storage 46 temporarily stores therein a signal calculated by the signal processor 44. The storage 46 may be, for example, a random access memory (RAM) or a register circuit.

The coordinate extractor 45 is a logic circuit that obtains, when the contact or the proximity of the finger is detected by the signal processor 44, detection coordinates of the asperities on the surface of, for example, the finger. The coordinate extractor 45 is also a logic circuit that obtains detected coordinates of blood vessels of the finger Fg or the palm. The image processor 49 combines the detection signals Vdet output from the respective photodiodes PD of the sensor 10 to generate two-dimensional information representing the shape of the asperities on the surface of, for example, the finger Fg and two-dimensional information representing a shape of the blood vessels of the finger Fg or the palm. The coordinate extractor 45 and the image processor 49 may be omitted.

The output processor 50 serves as a processor for performing processing based on the output from the photodiodes PD. Specifically, the output processor 50 of the embodiment outputs at least a sensor output Vo including at least pulse wave data based on the detection signal Vdet acquired through the signal processor 44. In the embodiment, the signal processor 44 outputs data indicating a variation (amplitude) in output of the detection signal Vdet of each of the photodiodes PD (to be described later), and the output processor 50 determines which output is to be employed as the sensor output Vo. However, the signal processor 44 or the output processor 50 may perform both the above-described operations. The output processor 50 may include, for example, the detected coordinates obtained by the coordinate extractor 45 and the two-dimensional information generated by the image processor 49 in the sensor output Vo. The function of the output processor 50 may be integrated in another component (for example, the image processor 49).

When the detection device of, for example, the pulse wave is mounted on a human body, noise is also detected associated with, for example, breathing, a change in attitude of the human body, and/or motion of the human body. Therefore, the signal processor 44 may be provided with a noise filter as required. The noise generated by the breathing and/or the change in attitude has frequency components of, for example, 1 Hz or lower, which are sufficiently lower than frequency components of the pulse wave. Therefore, the noise can be removed by using a band-pass filter as the noise filter. The band-pass filter may be provided, for example, in a detection signal amplifier 42. The frequency components of the noise generated by the motion of the human body are, for example, from several hertz to 100 hertz, and may overlap the frequency components of the pulse wave. In this case, however, the frequency is not constant and has a frequency fluctuation. Therefore, a noise filter is used that removes noise the frequencies of which have fluctuation components. As an example of a method for removing the frequencies having fluctuation components (first method for removing fluctuation components), a property may be used that a time lag of a peak value of the pulse wave occurs depending on the place of measurement of the human body. That is, the pulse wave has a time lag depending on the place of measurement of the human body, while the noise generated by the motion of the human body or the like has no time lag or a time lag smaller than that of the pulse wave. Therefore, the pulse wave is measured in at least two different places, and if peak values measured in the different places have occurred within a predetermined time, the pulse wave is removed as noise. Even in this case, a case can be considered where the waveform caused by noise accidentally overlaps the waveform caused by the pulse wave. However, in this case, the two waveforms overlap each other at only one place of the different places. Therefore, the waveform caused by noise can be distinguished from the waveform caused by the pulse wave. For example, the signal processor 44 can perform this processing. As another example of the method for removing the frequencies having fluctuation components (second method for removing fluctuation components), the signal processor 44 removes frequency components having different phases. In this case, for example, a short-time Fourier transform may be performed to remove the fluctuation components, and then, an inverse Fourier transform may be performed. Moreover, a commercial frequency power supply (50 Hz or 60 Hz) also serves as a noise source. However, in this case as well, in the same manner as the noise generated by the motion of the human body or other factors, the peak values measured at the different places have no time lag therebetween or a time lag therebetween smaller than that of the pulse wave. Therefore, the noise can be removed using the same method as the above-described first method for removing fluctuation components. Alternatively, the noise generated by the commercial frequency power supply may be removed by providing a shield on a surface on the opposite side of a detection surface of a detecting element.

Figure 4:
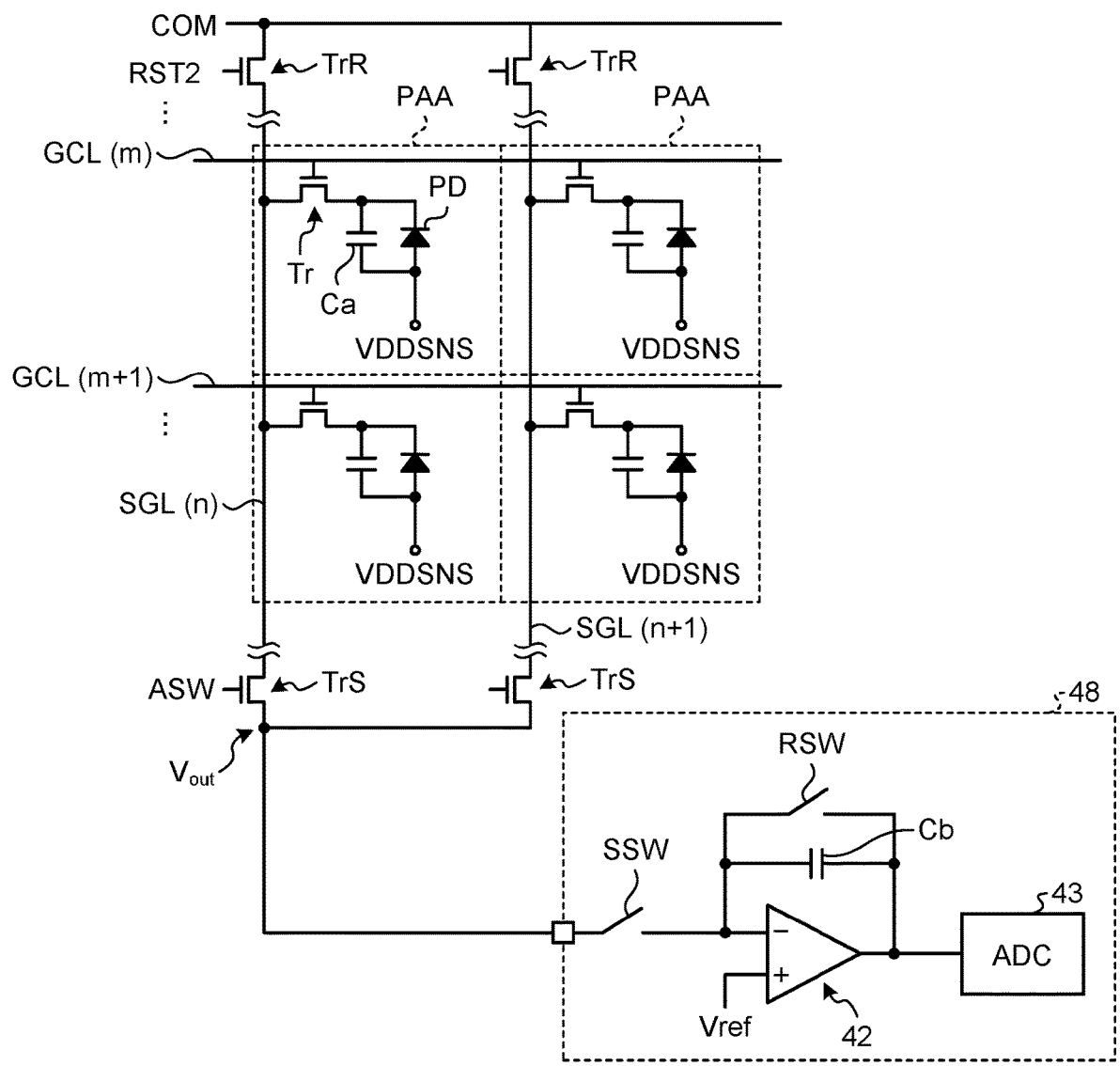
FIG. 4 is a circuit diagram illustrating a plurality of partial detection areas.

The following describes a circuit configuration example of the detection device 1. FIG. 3 is a circuit diagram illustrating the detection device. FIG. 4 is a circuit diagram illustrating a plurality of partial detection areas. FIG. 4 also illustrates a circuit configuration of the detection circuit 48.

As illustrated in FIG. 3, the sensor 10 has a plurality of partial detection areas PAA arranged in a matrix having a row-column configuration. Each of the partial detection areas PAA is provided with the photodiode PD.

The gate lines GCL extend in the first direction Dx, and are coupled to the partial detection areas PAA arranged in the first direction Dx. A plurality of gate lines GCL(1), GCL(2), ..., GCL(8) are arranged in the second direction Dy, and are each coupled to the gate line drive circuit 15. In the following description, the gate lines GCL(1), GCL(2), ..., GCL(8) will each be simply referred to as the gate line GCL when they need not be distinguished from one another. For ease of understanding of the description, FIG. 3 illustrates eight gate lines GCL. However, this is merely an example, and M gate lines GCL (where M is eight or larger, and is, for example, 256) may be arranged.

The signal lines SGL extend in the second direction Dy and are coupled to the photodiodes PD of the partial detection areas PAA arranged in the second direction Dy. A plurality of signal lines SGL(1), SGL(2), . . . , SGL(12) are arranged in the first direction Dx and are each coupled to the signal line selection circuit 16 and a reset circuit 17. In the following description, the signal lines SGL(1), SGL(2), . . . , SGL(12) will each be simply referred to as the signal line SGL when need not be distinguished from one another.

For ease of understanding of the description, 12 signal lines SGL are illustrated. However, this is merely an example, and N signal lines SGL (where N is 12 or larger, and is, for example, 252) may be arranged. The resolution of the sensor is, for example, 508 dots per inch (dpi), and the number of cells is 252×256. In FIG. 3, the sensor 10 is provided between the signal line selection circuit 16 and the reset circuit 17. The configuration is not limited thereto. The signal line selection circuit 16 and the reset circuit 17 may be coupled to ends of the signal lines SGL in the same direction. One sensor has an area of substantially 50×50 $\mu m^2$, for example. The detection area AA has an area of, for example, 12.6×12.8 $mm^2$.

The gate line drive circuit 15 receives the various control signals such as the start signal STV, the clock signal CK, and the reset signal RST1 from the control circuit 122 (refer to FIG. 1). The gate line drive circuit 15 sequentially selects the gate lines GCL(1), GCL(2), . . . , GCL(8) in a time-division manner based on the various control signals. The gate line drive circuit 15 supplies the gate drive signal Vgcl to the selected one of the gate lines GCL. This operation supplies the gate drive signal Vgcl to a plurality of first switching elements Tr coupled to the gate line GCL, and corresponding ones of the partial detection areas PAA arranged in the first direction Dx are selected as detection targets.

The gate line drive circuit 15 may perform different driving for each of detection modes including the detection of a fingerprint and the detection of different items of the biological information (such as the pulse wave, the pulsation, the blood vessel image, and the blood oxygen saturation level). For example, the gate line drive circuit 15 may drive more than one gate line GCL collectively.

Specifically, the gate line drive circuit 15 may simultaneously select a predetermined number of the gate lines GCL from among the gate lines GCL(1), GCL(2), . . . , GCL(8) based on the control signals. For example, the gate line drive circuit 15 simultaneously selects six gate lines GCL(1) to GCL(6) and supplies thereto the gate drive signals Vgcl. The gate line drive circuit 15 supplies the gate drive signals Vgcl through the selected six gate lines GCL to the first switching elements Tr. Through this operation, group areas PAG1 and PAG2 each including more than one partial detection area PAA arranged in the first direction Dx and the second direction Dy are selected as the respective detection targets. The gate line drive circuit 15 drives the predetermined number of the gate lines GCL collectively, and sequentially supplies the gate drive signals Vgcl to the gate lines GCL in units of the predetermined number of the gate lines GCL. Hereinafter, when positions of different group areas such as the group areas PAG1 and PAG2 are not distinguished from each other, each of the group areas will be called "group area PAG".

The signal line selection circuit 16 includes a plurality of selection signal lines Lsel, a plurality of output signal lines Lout, and third switching elements TrS. The third switching elements TrS are provided correspondingly to the signal lines SGL. Six signal lines SGL(1), SGL(2), . . . , SGL(6) are coupled to a common output signal line Lout1. Six signal lines SGL(7), SGL(8), . . . , SGL(12) are coupled to a common output signal line Lout2. The output signal lines Lout1 and Lout2 are each coupled to the detection circuit 48.

The signal lines SGL(1), SGL(2), . . . , SGL(6) are grouped into a first signal line block, and the signal lines SGL(7), SGL(8), . . . , SGL(12) are grouped into a second signal line block. The selection signal lines Lsel are coupled to the gates of the third switching elements TrS included in one of the signal line blocks, respectively. One of the selection signal lines Lsel is coupled to the gates of the third switching elements TrS in the signal line blocks.

Specifically, selection signal lines Lsel1, Lsel2, . . . , Lsel6 are coupled to the third switching elements TrS corresponding to the signal lines SGL(1), SGL(2), . . . , SGL(6), respectively. The selection signal line Lsel1 is coupled to the third switching element TrS corresponding to the signal line SGL(1) and the third switching element TrS corresponding to the signal line SGL(7). The selection signal line Lsel2 is coupled to the third switching element TrS corresponding to the signal line SGL(2) and the third switching element TrS corresponding to the signal line SGL(8).

The control circuit 122 (refer to FIG. 1) sequentially supplies the selection signal ASW to the selection signal lines Lsel. Through the operations of the third switching elements TrS, the signal line selection circuit 16 sequentially selects the signal lines SGL in one of the signal line blocks in a time-division manner. The signal line selection circuit 16 selects one of the signal lines SGL in each of the signal line blocks. With the above-described configuration, the detection device 1 can reduce the number of integrated circuits (ICs) including the detection circuit 48 or the number of terminals of the ICs.

The signal line selection circuit 16 may couple more than one signal line SGL to the detection circuit 48 collectively. Specifically, the control circuit 122 (refer to FIG. 1) simultaneously supplies the selection signal ASW to the selection signal lines Lsel. With this operation, the signal line selection circuit 16 selects, by the operations of the third switching elements TrS, the signal lines SGL (for example, six signal lines SGL) in one of the signal line blocks, and couples the signal lines SGL to the detection circuit 48. As a result, signals detected in each group area PAG are output to the detection circuit 48. In this case, signals from the partial detection areas PAA (photodiodes PD) in each group area PAG are put together and output to the detection circuit 48.

By the operations of the gate line drive circuit 15 and the signal line selection circuit 16, the detection is performed for each group area PAG. As a result, the intensity of the detection signal Vdet obtained by one time of detection increases, so that the sensor sensitivity can be improved. In addition, time required for the detection can be reduced. Consequently, the detection device 1 can repeatedly perform the detection in a short time, and thus, can improve a signal-to-noise (S/N) ratio, and can accurately detect a change in the biological information with time, such as the pulse wave.

As illustrated in FIG. 3, the reset circuit 17 includes a reference signal line Lvr, a reset signal line Lrst, and fourth switching elements TrR. The fourth switching elements TrR are provided correspondingly to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference signal COM to the reference signal line Lvr. This operation supplies the reference signal COM to a capacitive element Ca (refer to FIG. 4) included in each of the partial detection areas PAA.

As illustrated in FIG. 4, each of the partial detection areas PAA includes the photodiode PD, the capacitive element Ca, and the first switching element Tr. FIG. 4 illustrates two gate lines GCL(m) and GCL(m+1) arranged in the second direction Dy among the gate lines GCL and illustrates two signal lines SGL(n) and SGL(n+1) arranged in the first direction Dx among the signal lines SGL. The partial detection area PAA is an area surrounded by the gate lines GCL and the signal lines SGL. Each of the first switching elements Tr is provided correspondingly to each of the photodiodes PD. The first switching element Tr includes a thin-film transistor, and in this example, includes an n-channel metal oxide semiconductor (MOS) thin-film transistor (TFT).

The gates of the first switching elements Tr belonging to the partial detection areas PAA arranged in the first direction Dx are coupled to the gate line GCL. The sources of the first switching elements Tr belonging to the partial detection areas PAA arranged in the second direction Dy are coupled to the signal line SGL. The drain of the first switching element Tr is coupled to the cathode of the photodiode PD and the capacitive element Ca.

The anode of the photodiode PD is supplied with the sensor power supply signal VDDSNS from the power supply circuit 123. The signal line SGL and the capacitive element Ca are supplied with the reference signal COM that serves as an initial potential of the signal line SGL and the capacitive element Ca from the power supply circuit 123.

When the partial detection area PAA is irradiated with light, a current corresponding to an amount of light flows through the photodiode PD. As a result, an electrical charge is stored in the capacitive element Ca. After the first switching element Tr is turned on, a current corresponding to the electrical charge stored in the capacitive element Ca flows through the signal line SGL. The signal line SGL is coupled to the detection circuit 48 through a corresponding one of the third switching elements TrS of the signal line selection circuit 16. Thus, the detection device 1 can detect a signal corresponding to an amount of the light irradiating the photodiode PD in each of the partial detection areas PAA or signals corresponding to the amounts of the light irradiating the photodiodes PD in each group area PAG.

During a reading period Pdet (refer to FIG. 7), a switch SSW of the detection circuit 48 is turned on, and the detection circuit 48 is coupled to the signal lines SGL. The detection signal amplifier 42 of the detection circuit 48 converts a variation of a current supplied from the signal lines SGL into a variation of a voltage, and amplifies the result. A reference potential (Vref) having a fixed potential is supplied to a non-inverting input portion (+) of the detection signal amplifier 42, and the signal lines SGL are coupled to an inverting input portion (−) of the detection signal amplifier 42. In the first embodiment, the same signal as the reference signal COM is supplied as a reference potential (Vref). The detection signal amplifier 42 includes a capacitive element Cb and a reset switch RSW. During a reset period Prst (refer to FIG. 7), the reset switch RSW is turned on, and an electrical charge of the capacitive element Cb is reset.

Figure 5:
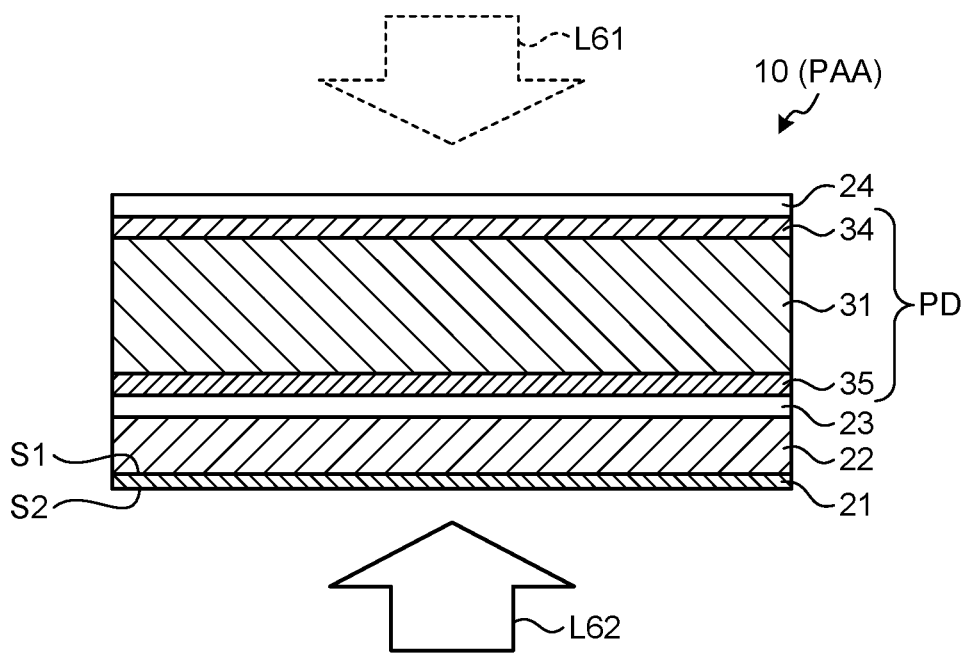
FIG. 5 is sectional view illustrating a schematic sectional configuration of a sensor.
Figure 6:
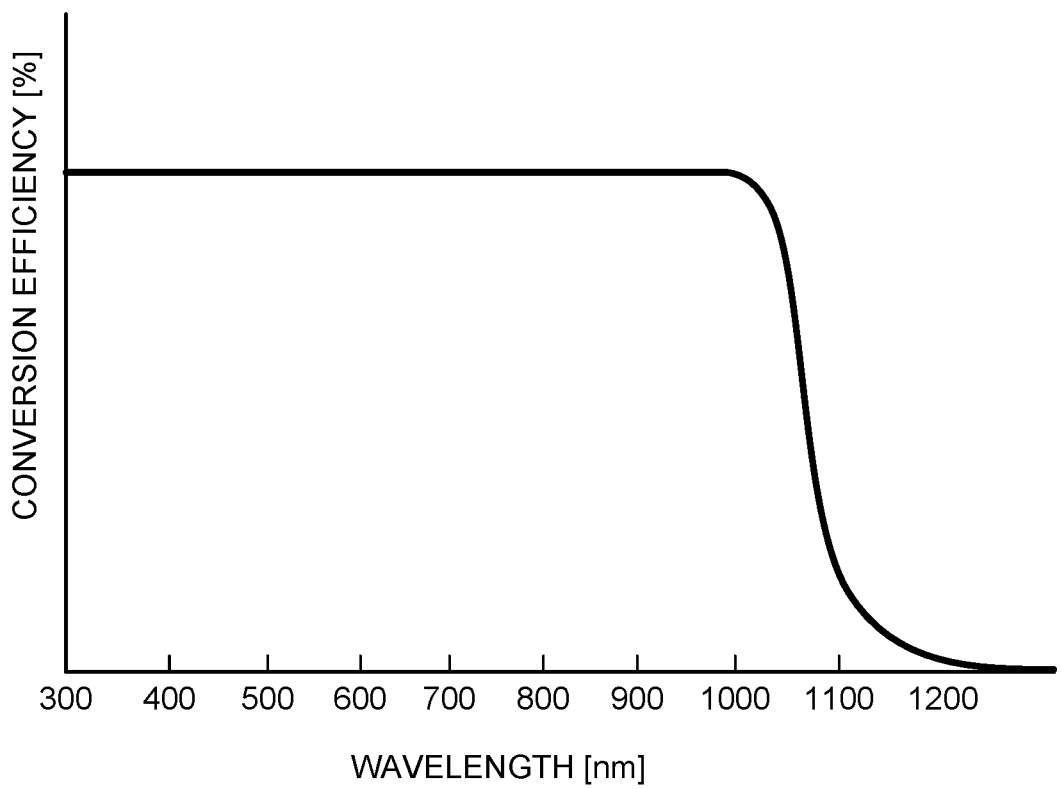
FIG. 6 is a graph schematically illustrating a relation between a wavelength and a conversion efficiency of light incident on a photodiode.

The following describes a configuration of the photodiode PD. FIG. 5 is a sectional view illustrating a schematic sectional configuration of the sensor. FIG. 6 is a graph schematically illustrating a relation between the wavelength and a conversion efficiency of light incident on the photodiode.

As illustrated in FIG. 5, the sensor 10 includes the sensor base member 21, a TFT layer 22, an insulating layer 23, the photodiode PD, and a protection film 24. The sensor base member 21 is an insulating base member and is made using, for example, glass or resin material. The sensor base member 21 is not limited to having a flat plate shape, and may have a curved surface. In this case, the sensor base member 21 may be formed of a film-shaped resin. The sensor base member 21 has a first surface S1 and a second surface S2 on the opposite side of the first surface S1. The TFT layer 22, the insulating layer 23, the photodiode PD, and the protection film 24 are stacked on the first surface S1 in the order as listed.

The TFT layer 22 is used for circuits such as the gate line drive circuit 15 and the signal line selection circuit 16 described above. The TFT layer 22 is also provided with thin-film transistors (TFTs), such as the first switching element Tr, and various types of wiring, such as the gate lines GCL and the signal lines SGL. The sensor base member 21 and the TFT layer 22, which serve as a drive circuit board that drives the sensor for each predetermined detection area, are also called a backplane.

The insulating layer 23 is an inorganic insulating layer. For example, an oxide such as silicon oxide ($SiO_2$) or a nitride such as silicon nitride (SiN) is used as the insulating layer 23.

The photodiode PD is provided on the insulating layer 23. The photodiode PD includes a photoelectric conversion layer 31, a cathode electrode 35, and an anode electrode 34. The cathode electrode 35, the photoelectric conversion layer 31, and the anode electrode 34 are stacked in the order as listed, in a direction orthogonal to the first surface S1 of the sensor base member 21. The stacking order in the photodiode PD may be as follows: the anode electrode 34, the photoelectric conversion layer 31, and the cathode electrode 35.

Characteristics (such as a voltage-current characteristic and a resistance value) of the photoelectric conversion layer 31 vary depending on the irradiated light. An organic material is used as the material of the photoelectric conversion layer 31. Specifically, a low-molecular organic material such as $C_{60}$ (fullerene), phenyl-$C_{61}$-butyric acid methyl ester (PCBM), copper phthalocyanine (CuPc), fluorinated copper phthalocyanine ($F_{16}$CuPc), rubrene (5,6,11,12-tetraphenyltetracene), or PDI (derivative of perylene) can be used as the photoelectric conversion layer 31.

The photoelectric conversion layer 31 can be formed by a vapor deposition method (dry process) using any of the above-listed low-molecular organic materials. In this case, the photoelectric conversion layer 31 may be a laminated film of CuPc and $F_{16}$CuPc, or a laminated film of rubrene and $C_{60}$. The photoelectric conversion layer 31 can also be formed by an application method (wet process). In this case, a material obtained by combining any of the above-listed low-molecular organic materials with a polymeric organic material is used as the photoelectric conversion layer 31. For example, poly(3-hexylthiophene) (P3HT) or F8-alt-benzothiadiazole (F8BT) can be used as the polymeric organic material. The photoelectric conversion layer 31 can be a film in a state of a mixture of P3HT and PCBM, or a film in a state of a mixture of F8BT and PDI.

The cathode electrode 35 faces the anode electrode 34 with the photoelectric conversion layer 31 interposed therebetween. A light-transmitting conductive material such as indium tin oxide (ITO) is used as the anode electrode 34. A metal material such as silver (Ag) or aluminum (Al) is used as the cathode electrode 35. Alternatively, the cathode electrode 35 may be an alloy material containing at least one or more of these metal materials.

The cathode electrode 35 can be formed as a light-transmitting transflective electrode by controlling the film thickness of the cathode electrode 35. For example, the cathode electrode 35 is formed of a Ag thin film having a film thickness of 10 nm so as to have light transmittance of approximately 60%. In this case, the photodiode PD can detect light emitted from both surface sides of the sensor base member 21, for example, both the first light L61 emitted from the first surface S1 side and the second light L62 emitted from the second surface S2 side.

The protection film 24 is provided so as to cover the anode electrode 34. The protection film 24 is a passivation film and is provided to protect the photodiode PD.

The horizontal axis of the graph illustrated in FIG. 6 represents the wavelength of the light incident on the photodiode PD, and the vertical axis of the graph represents an external quantum efficiency of the photodiode PD. The external quantum efficiency is expressed as a ratio between the number of photons of the light incident on the photodiode PD and a current that flows from the photodiode PD to the external detection circuit 48.

As illustrated in FIG. 6, the photodiode PD has an excellent efficiency in a wavelength range from approximately 300 nm to approximately 1000 nm. That is, the photodiode PD has a sensitivity for wavelengths of both the first light L61 emitted from the first light sources 61 and the second light L62 emitted from the second light sources 62. Therefore, each of the photodiodes PD can detect a plurality of beams of light having different wavelengths.

Figure 7:
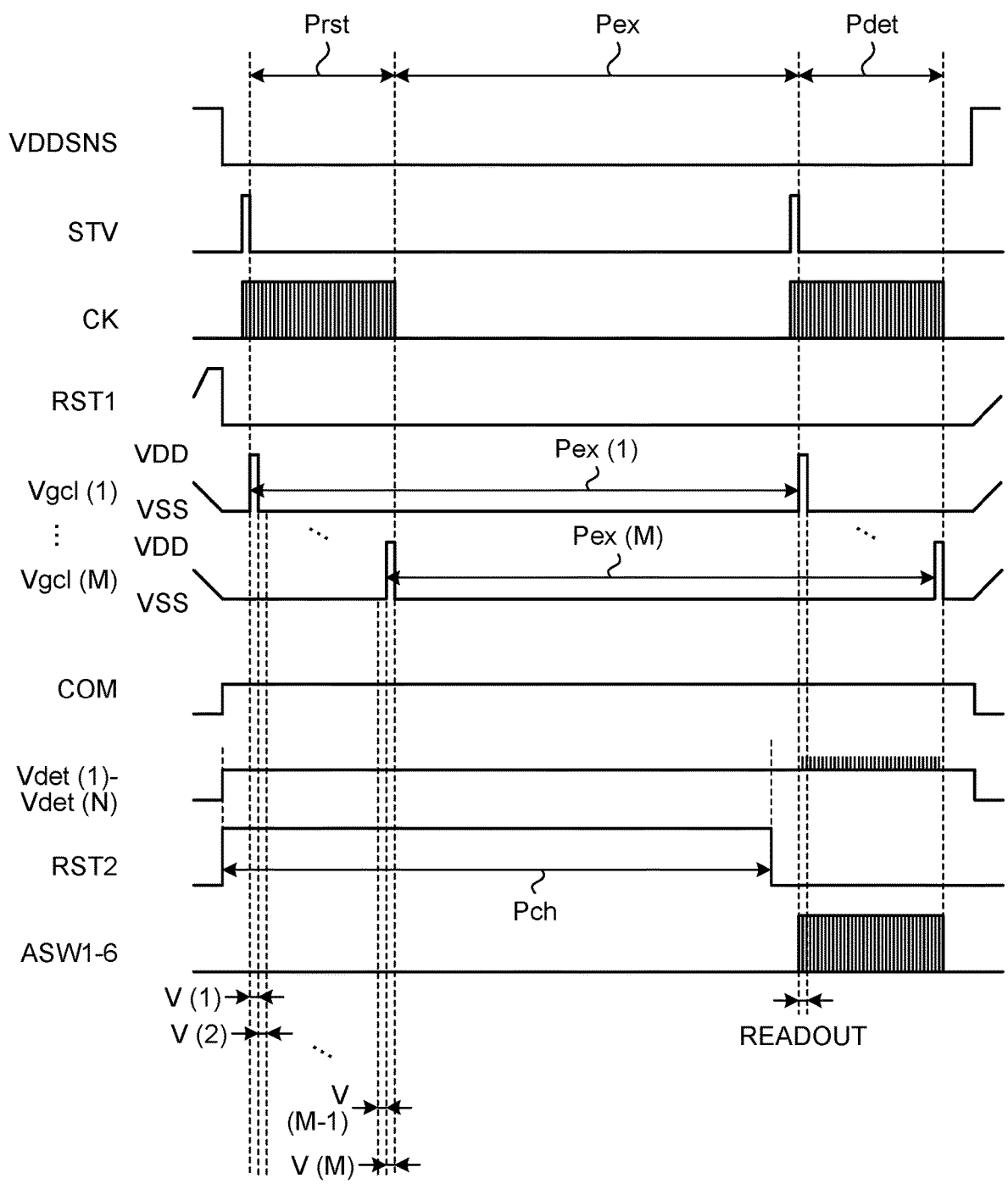
FIG. 7 is a timing waveform diagram illustrating an operation example of the detection device.

The following describes an operation example of the detection device 1. FIG. 7 is a timing waveform diagram illustrating the operation example of the detection device. As illustrated in FIG. 7, the detection device 1 has the reset period Prst, an effective exposure period Pex, and the reading period Pdet. The power supply circuit 123 supplies the sensor power supply signal VDDSNS to the anode of the photodiode PD over the reset period Prst, the effective exposure period Pex, and the reading period Pdet. The sensor power supply signal VDDSNS is a signal for applying a reverse bias between the anode and the cathode of the photodiode PD. For example, the reference signal COM of substantially 0.75 V is applied to the cathode of the photodiode PD, and the sensor power supply signal VDDSNS of substantially −1.25 V is applied to the anode of the photodiode PD. As a result, a reverse bias of substantially 2.0 V is applied between the anode and the cathode. At the time of detection of a wavelength of 850 nm, the reverse bias of 2 V is applied to the photodiode PD so as to obtain a high sensitivity of 0.5 A/W to 0.7 A/W, preferably approximately 0.57 A/W. The following characteristics of the photodiode are used: the dark current density is $1.0 \times 10^{-7}$ A/cm$^2$ when the reverse bias of 2 V is applied, and the photocurrent density is $1.2 \times 10^{-3}$ A/cm$^2$ when light having an output of substantially 2.9 mW/cm$^2$ and a wavelength of 850 nm is detected. The external quantum efficiency (EQE) is approximately 1.0 when the reverse bias of 2 V is applied at the time when the photodiode is irradiated with the light having a wavelength of 850 nm. The control circuit 122 sets the reset signal RST2 to "H", and then, supplies the start signal STV and the clock signal CK to the gate line drive circuit 15 to start the reset period Prst. During the reset period Prst, the control circuit 122 supplies the reference signal COM to the reset circuit 17 and uses the reset signal RST2 to turn on the fourth switching elements TrR for supplying a reset voltage. This operation supplies the reference signals COM as the reset voltage to the signal lines SGL. The reference signal COM is set to, for example, 0.75 V.

During the reset period Prst, the gate line drive circuit 15 sequentially selects each of the gate lines GCL based on the start signal STV, the clock signal CK, and the reset signal RST1. The gate line drive circuit 15 sequentially supplies the gate drive signals Vgcl {Vgcl(1) to Vgcl(M)} to the gate lines GCL. The gate drive signal Vgcl has a pulsed waveform having a power supply voltage VDD serving as a high-level voltage and a power supply voltage VSS serving as a low-level voltage. In FIG. 7, M gate lines GCL (where M is, for example, 256) are provided, and the gate drive signals Vgcl(1) . . . , Vgcl(M) are sequentially supplied to the respective gate lines GCL. Thus, the first switching elements Tr are sequentially brought into a conducting state and supplied with the reset voltage on a row-by-row basis. For example, a voltage of 0.75 V of the reference signal COM is supplied as the reset voltage.

Thus, during the reset period Prst, the capacitive elements Ca of all the partial detection areas PAA are sequentially electrically coupled to the signal lines SGL, and are supplied with the reference signal COM. As a result, the electrical charges stored in the capacitance of the capacitive elements Ca are reset. The capacitance of the capacitive elements Ca of some of the partial detection areas PAA can be reset by partially selecting the gate lines and the signal lines SGL.

Examples of the exposure timing control method include a control method of exposure during scanning time of gate line and a full-time control method of exposure. In the control method of exposure during scanning time of gate line, the gate drive signals {Vgcl(1) to Vgcl(M)} are sequentially supplied to all the gate lines GCL coupled to the photodiodes PD serving as the detection targets, and all the photodiodes PD serving as the detection targets are supplied with the reset voltage. Then, after all the gate lines GCL coupled to the photodiodes PD serving as the detection targets are set to a low voltage (the first switching elements Tr are turned off), the exposure starts, whereby the exposure is performed during the effective exposure period Pex. After the exposure ends, the gate drive signals {Vgcl(1) to Vgcl(M)} are sequentially supplied to the gate lines GCL coupled to the photodiodes PD serving as the detection targets as described above and reading is performed during the reading period Pdet. In the full-time control method of exposure, control for performing the exposure can also be performed during the reset period Prst and the reading period Pdet (full-time exposure control). In this case, the effective exposure period Pex(1) starts after the gate drive signal Vgcl(M) is supplied to the gate line GCL. The term "effective exposure periods Pex{(1), . . . , (M)}" refers to a period during which the capacitive elements Ca are charged from the photodiodes PD. The start timing and the end timing of the actual effective exposure periods Pex(1), . . . , Pex(M) are different among the partial detection areas PAA corresponding to the gate lines GCL. Each of the effective exposure periods Pex(1), . . . , Pex(M) starts when the gate drive signal Vgcl changes from the power supply voltage VDD serving as the high-level voltage to the power supply voltage VSS serving as the low-level voltage during the reset period Prst. Each of the effective exposure periods Pex(1), . . . , Pex(M) ends when the gate drive signal Vgcl changes from the power supply voltage VSS to the power supply voltage VDD during the reading period Pdet. The lengths of the exposure time of the effective exposure periods Pex(1), ..., Pex(M) are equal.

In the control method of exposure during scanning time of gate line, a current flows corresponding to the light irradiating the photodiode PD in each of the partial detection areas PAA during the effective exposure periods Pex. As a result, an electrical charge is stored in each of the capacitive elements Ca.

At a time before the reading period Pdet starts, the control circuit 122 sets the reset signal RST2 to a low-level voltage. This operation stops operation of the reset circuit 17. The reset signal may be set to a high-level voltage only during the reset period Prst. During the reading period Pdet, the gate line drive circuit 15 sequentially supplies the gate drive signals Vgcl(1) ..., Vgcl(M) to the gate lines GCL in the same manner as during the reset period Prst.

Specifically, the gate line drive circuit 15 supplies the gate drive signal Vgcl(1) at the high-level voltage (power supply voltage VDD) to the gate line GCL(1) during a period V(1). The control circuit 122 sequentially supplies the selection signals ASW1, ..., ASW6 to the signal line selection circuit 16 during a period in which the gate drive signal Vgcl(1) is at the high-level voltage (power supply voltage VDD). This operation sequentially or simultaneously couples the signal lines SGL of the partial detection areas PAA selected by the gate drive signal Vgcl(1) to the detection circuit 48. As a result, the detection signal Vdet for each of the partial detection areas PAA is supplied to the detection circuit 48. A time of, for example, approximately 20 s (substantially 20 s) elapses from when the gate drive signal Vgcl(1) is set to the high level to when the first selection signal ASW1 starts to be supplied, and a time of, for example, approximately 60 s (substantially 60 s) elapses while each of the selection signals ASW1, ..., ASW6 is supplied. Such a high-speed response can be achieved by using thin-film transistors (TFTs) made using low-temperature polysilicon (LTPS) having mobility of substantially 40 cm$^2$/Vs.

In the same manner, the gate line drive circuit 15 supplies the gate drive signals Vgcl(2), ..., Vgcl(M−1), Vgcl(M) at the high-level voltage to gate lines GCL(2), ..., GCL(M−1), GCL(M) during periods V(2), ..., V(M−1), V(M), respectively. That is, the gate line drive circuit 15 supplies the gate drive signal Vgcl to the gate line GCL during each of the periods V(1), V(2), ..., V(M−1), V(M). The signal line selection circuit 16 sequentially selects each of the signal lines SGL based on the selection signal ASW in each period in which the gate drive signal Vgcl is set to the high-level voltage. The signal line selection circuit 16 sequentially couples each of the signal lines SGL to one detection circuit 48. Thus, the detection device 1 can output the detection signals Vdet of all the partial detection areas PAA to the detection circuit 48 during the reading period Pdet.

Figure 8:
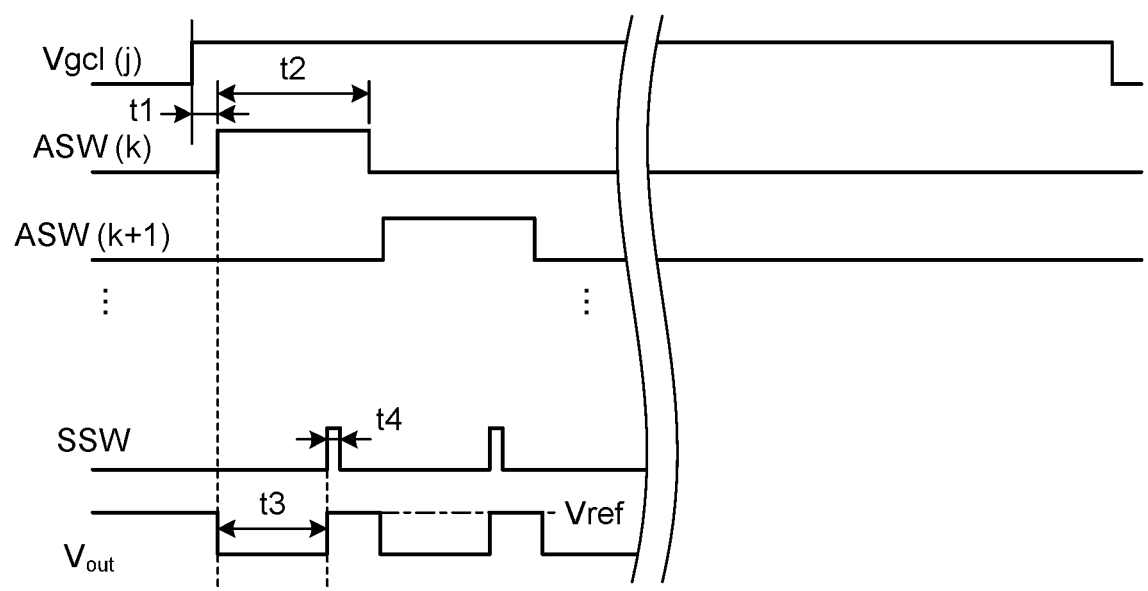
FIG. 8 is a timing waveform diagram illustrating an operation example during a reading period in FIG. 7.

FIG. 8 is a timing waveform diagram illustrating an operation example during a drive period of one of the gate lines included in a reading period Readout in FIG. 7. With reference to FIG. 8, the following describes the operation example during the supply period Readout of one of the gate drive signals Vgcl(j) in FIG. 7. In FIG. 7, the reference numeral of the supply period "Readout" is assigned to the first gate drive signal Vgcl(1), but the same applies to the other gate drive signals Vgcl(2) ..., Vgcl(M). The index j is any one of the natural numbers 1 to M.

As illustrated in FIGS. 8 and 4, an output ($V_{out}$) of each of the third switching elements TrS has been reset to the reference potential (Vref) in advance. The reference potential (Vref) serves as a reset voltage, and is set to, for example, 0.75 V. Then, the gate drive signal Vgcl(j) is set to a high level, and the first switching elements Tr of a corresponding row are turned on. Thus, each of the signal lines SGL of each row is set to a voltage corresponding to the electrical charge stored in the capacitor (capacitive element Ca) of the partial detection area PAA. After a period t1 elapses from a rise of the gate drive signal Vgcl(j), a period t2 starts in which the selection signal ASW(k) is set to a high level. After the selection signal ASW(k) is set to the high level and the third switching element TrS is turned on, the output ($V_{out}$) of the third switching element TrS (refer to FIG. 4) is changed to a voltage corresponding to the electrical charge stored in the capacitor (capacitive element Ca) of the partial detection area PAA coupled to the detection circuit 48 through the third switching element TrS, by the electrical charge stored in the capacitor (capacitive element Ca) of the partial detection area PAA (period t3). In the example of FIG. 8, this voltage is reduced from the reset voltage as illustrated in the period t3. Then, after the switch SSW is turned on (high-level period t4 of an SSW signal), the electrical charge stored in the capacitor (capacitive element Ca) of the partial detection area PAA moves to a capacitor (capacitive element Cb) of the detection signal amplifier 42 of the detection circuit 48, and the output voltage of the detection signal amplifier 42 is set to a voltage corresponding to the electrical charge stored in the capacitive element Cb. At this time, the potential of an inverting input portion of the detection signal amplifier 42 is set to an imaginary short-circuit potential of the operational amplifier, and therefore, returns to the reference potential (Vref). The A/D converter 43 reads the output voltage of the detection signal amplifier 42. In the example of FIG. 8, waveforms of the selection signals ASW(k), ASW(k+1), ... corresponding to the signal lines SGL of the respective columns are set to be a high level to sequentially turn on the third switching elements TrS, and the same operation is sequentially performed. This operation sequentially reads the electrical charges stored in the capacitors (capacitive elements Ca) of the partial detection areas PAA coupled to the gate line GCL. ASW(k), ASW(k+1), ... in FIG. 8 are, for example, any of ASW 1 to 6 in FIG. 7.

Specifically, after the period t4 starts in which the switch SSW is on, the electrical charge moves from the capacitor (capacitive element Ca) of the partial detection area PAA to the capacitor (capacitive element Cb) of the detection signal amplifier 42 of the detection circuit 48. At this time, the non-inverting input (+) of the detection signal amplifier 42 is biased to the reference potential (Vref) (for example, 0.75 (V)). As a result, the output ($V_{out}$) of the third switching element TrS is also set to the reference potential (Vref) due to the imaginary short-circuit between input ends of the detection signal amplifier 42. The voltage of the capacitive element Cb is set to a voltage corresponding to the electrical charge stored in the capacitor (capacitive element Ca) of the partial detection area PAA at a location where the third switching element TrS is turned on in response to the selection signal ASW(k). After the output ($V_{out}$) of the third switching element TrS is set to the reference potential (Vref) due to the imaginary short-circuit, the output of the detection signal amplifier 42 reaches a capacitance corresponding to the voltage of the capacitive element Cb, and this output voltage is read by the A/D converter 43. The voltage of the capacitive element Cb is, for example, a voltage between two electrodes in a capacitor constituting the capacitive element Cb.

The period t1 is, for example, 20 (s). The period t2 is, for example, 60 (s). The period t3 is, for example, 44.7 (s). The period t4 is, for example, 0.98 (s).

Although FIGS. 7 and 8 illustrate the example in which the gate line drive circuit 15 selects the gate line GCL individually, the number of the gate lines GCL to be selected is not limited to this example. The gate line drive circuit 15 may simultaneously select a predetermined number (two or more) of the gate lines GCL and sequentially supply the gate drive signals Vgcl to the gate lines GCL in units of the predetermined number of the gate lines GCL. The signal line selection circuit 16 may also simultaneously couple a predetermined number (two or more) of the signal lines SGL to one detection circuit 48. Moreover, the gate line drive circuit 15 may skip some of the gate lines GCL and scan the remaining ones. The dynamic range is, for example, approximately $10^3$ when the effective exposure period Pex is approximately 4.3 ms. A high resolution can be achieved by setting the frame rate to approximately 4.4 fps (substantially 4.4 fps).

The detection device 1 can detect a fingerprint based on capacitance. Specifically, the capacitive element Ca is used. First, all the capacitive elements Ca are each charged with a predetermined electrical charge. Then, a finger Fg touches the detection area AA, and thereby, capacitance corresponding to the asperities of the fingerprint is added to the capacitive element Ca of each of the cells. Thus, a fingerprint pattern can be generated by using the detection signal amplifier 42 and the A/D converter 43 to read the capacitance represented by the output from the capacitive element Ca of each of the cells in the state where the finger Fg in contact with the detection area AA in the same manner as the acquisition of the output from each of the partial detection areas PAA described with reference to FIGS. 7 and 8. This method allows a fingerprint to be detected using a capacitance method. A structure is preferably employed in which the distance between the capacitor of the partial detection area PAA and an object to be detected such as a fingerprint is set in a range from 100 μm to 300 μm.

Figure 9:
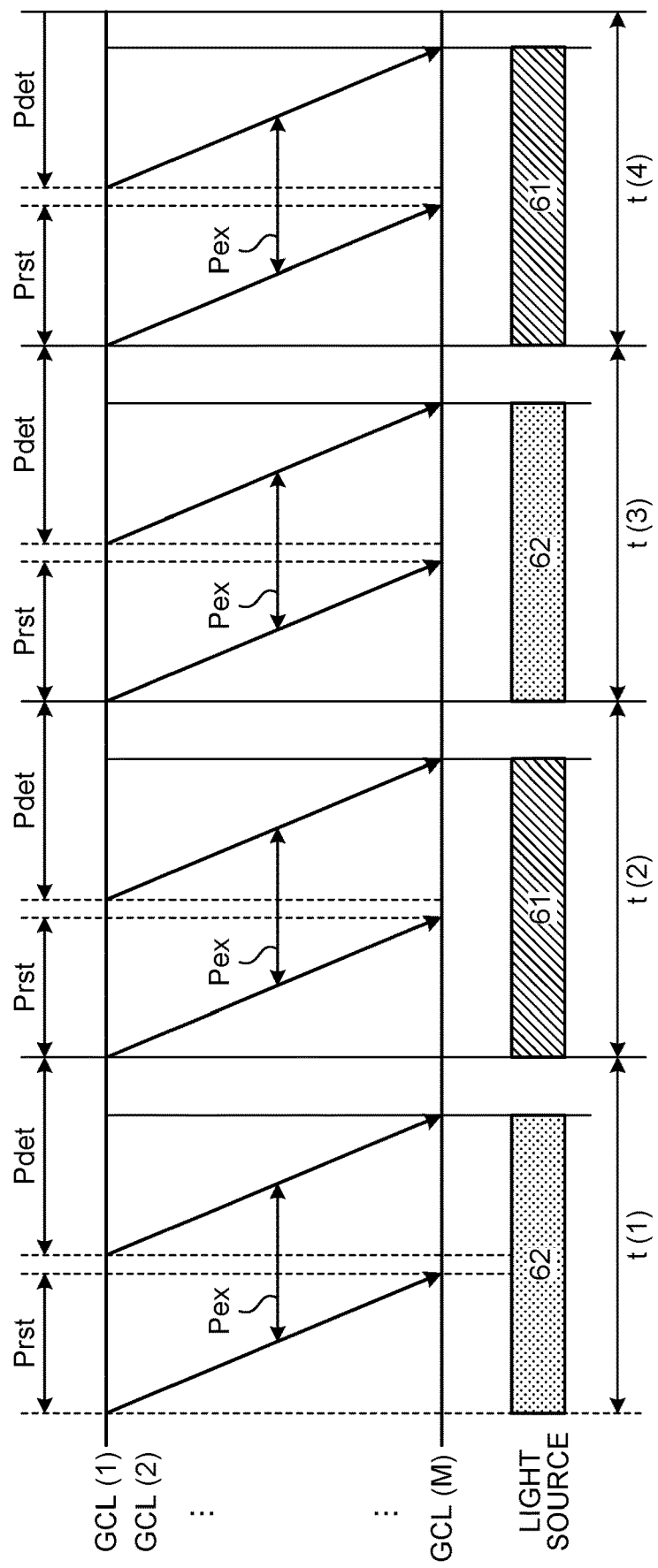
FIG. 9 is an explanatory diagram for explaining a relation between driving of the sensor and lighting operations of light sources in the detection device.

The following describes an operation example of the sensor 10, the first light sources 61, and the second light sources 62. FIG. 9 is an explanatory diagram for explaining a relation between driving of the sensor and lighting operations of the light sources in the detection device.

As illustrated in FIG. 9, during each of the periods t(1) to t(4), the detection device 1 performs the processing in the reset period Prst, the effective exposure period Pex{(1), . . . , (M)}, and the reading period Pdet described above. During the reset period Prst and the reading period Pdet, the gate line drive circuit 15 sequentially performs scanning from the gate line GCL(1) to the gate line GCL (M).

During the period t(1), the second light sources 62 are on, and the first light sources 61 are off. As a result, in the detection device 1, currents flow from the photodiodes PD through the signal lines SGL to the detection circuit 48 based on the second light L62 emitted from the second light sources 62. During the period t(2), the first light sources 61 are on, and the second light sources 62 are off. As a result, in the detection device 1, currents flow from the photodiodes PD through the signal lines SGL to the detection circuit 48 based on the first light L61 emitted from the first light sources 61. In the same manner, during the period t(3), the second light sources 62 are on, and the first light sources 61 are off; and during the period t(4), the first light sources 61 are on, and the second light sources 62 are off.

In this manner, the first light sources 61 and the second light sources 62 are caused to be on in a time-division manner at intervals of the period t. This operation outputs the first detection signals detected by the photodiodes PD based on the first light L61 and the second detection signals detected by the photodiodes PD based on the second light L62 to the detection circuit 48 in a time-division manner. Consequently, the first detection signals and the second detection signals are restrained from being output to the detection circuit 48 in a mutually superimposed manner. As a result, the detection device 1 can well detect the various types of the biological information.

The driving method of the first light sources 61 and the second light sources 62 can be changed as appropriate. For example, in FIG. 9, the first light sources 61 and the second light sources 62 are alternately caused to be on at intervals of the period t. However, the driving method is not limited thereto. The first light sources 61 may be turned on in successive periods t, and then, the second light sources 62 may be turned on in successive periods t. The first light sources 61 and the second light sources 62 may be simultaneously turned on in each period t. FIG. 9 illustrates an example of the full-time control method of exposure. However, also in the control method of exposure during scanning time of gate line, the first light sources 61 and the second light sources 62 may be alternately driven at intervals of the period t in the same manner as illustrated in FIG. 9.

Figure 10:
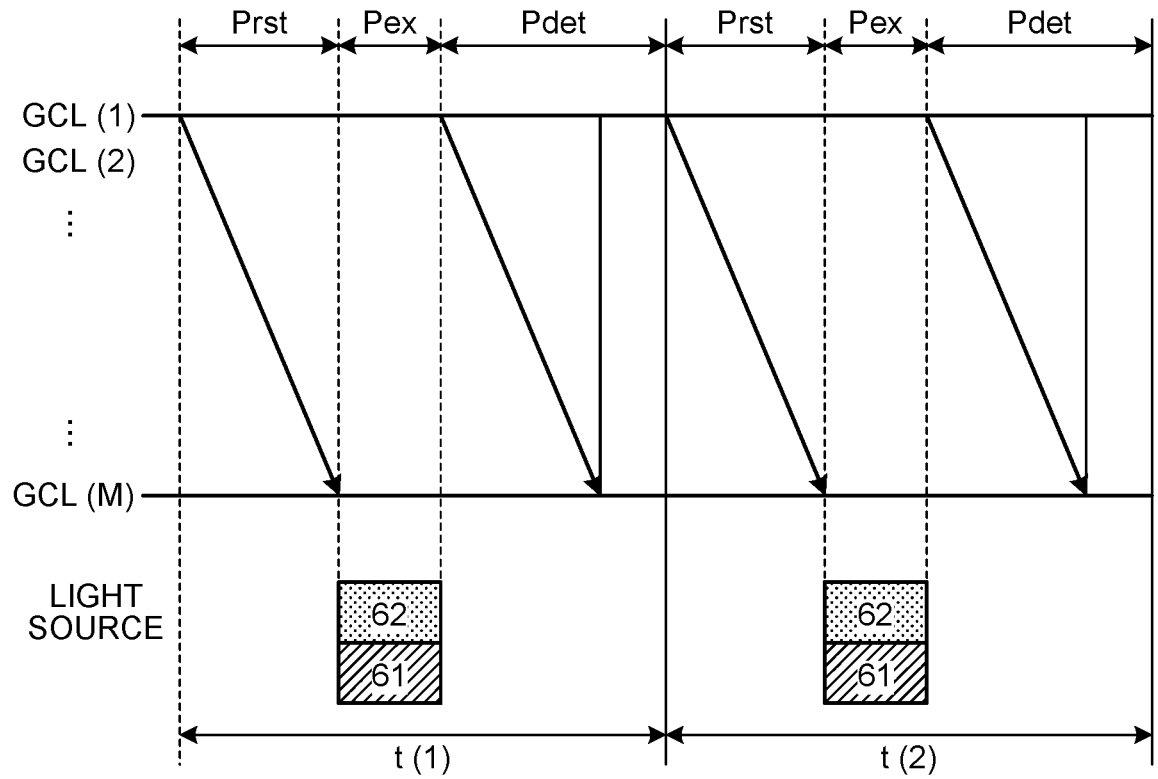
FIG. 10 is an explanatory diagram for explaining a relation between the driving of the sensor and the lighting operations of the light sources according to a first modification of the first embodiment.

FIG. 10 is an explanatory diagram for explaining a relation between the driving of the sensor and the lighting operations of the light sources different from the relation of FIG. 9. In the example illustrated in FIG. 10, the first light sources 61 and the second light sources 62 are on during the effective exposure period Pex, and are off during the reset period Prst and the reading period Pdet. Through these operations, the detection device 1 can reduce power consumption required for the detection.

The lighting operations are not limited to the example illustrated in FIG. 10. The first light sources 61 and the second light sources 62 may be continuously turned on over all the periods including the reset period Prst, the effective exposure period Pex, and the reading period Pdet. Either the first light sources 61 or the second light sources 62 may be on during the effective exposure period Pex, and the first light sources 61 and the second light sources 62 may be alternately on at intervals of the period t.

Figure 11:
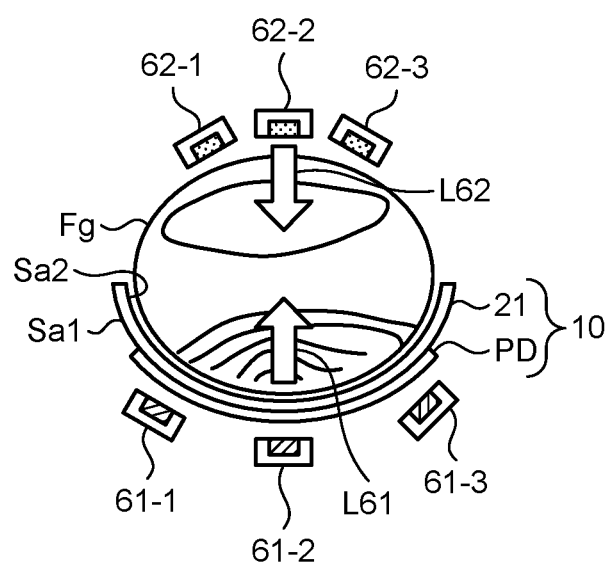
FIG. 11 is a cross sectional view schematically illustrating a relation between the sensor and first and second light sources of the detection device according to the first embodiment.
Figure 12:
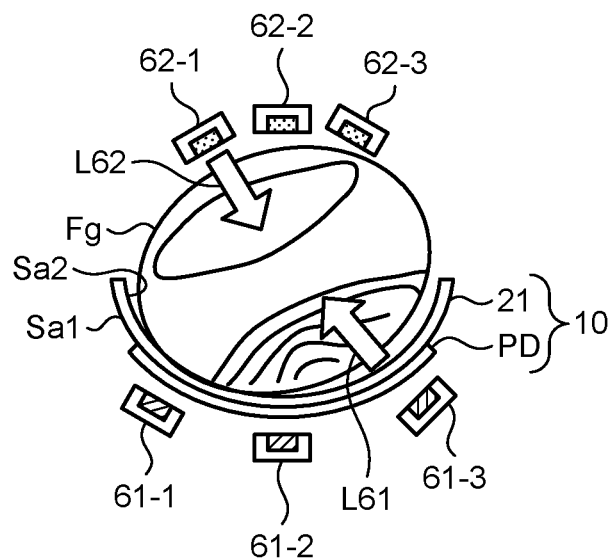
FIG. 12 is another cross sectional view schematically illustrating the relation between the sensor and the first and second light sources of the detection device according to the first embodiment.

FIGS. 11 and 12 are cross sectional views schematically illustrating a relation between the sensor and the first and second light sources of the detection device according to the first embodiment. FIGS. 11 and 12 illustrate operation examples when relative positional relations between the finger Fg and the sensor 10 differ. As illustrated in FIGS. 11 and 12, the sensor base member 21 has a first curved surface Sa1 and a second curved surface Sa2 on the opposite side of the first curved surface Sa1. The first curved surface Sa1 is curved in a convex manner in a direction from the second curved surface Sa2 toward the first curved surface Sa1. The second curved surface Sa2 is curved in a concave manner along the surface of the finger Fg. The first curved surface Sa1 is provided with the photodiodes PD. The sensor base member 21 may be of a light-transmitting film-shaped resin material, or may be a curved glass substrate.

A plurality of first light sources 61-1, 61-2, and 61-3 are provided along the first curved surface Sa1, and emit the first light L61 in different directions. A plurality of second light sources 62-1, 62-2, and 62-3 are provided so as to face the second curved surface Sa2, and emit the second light L62 in different directions. The first light source 61-1 and the second light source 62-3 are arranged so as to interpose the finger Fg therebetween, and emit the first light L61 and the second light L62 in the opposite directions. In the same manner, the first light source 61-2 and the second light source 62-2 are arranged so as to interpose the finger Fg therebetween, and emit the first light L61 and the second light L62 in the opposite directions. The first light source 61-3 and the second light source 62-1 are arranged so as to interpose the finger Fg therebetween, and emit the first light L61 and the second light L62 in the opposite directions.

In the following description, the first light sources 61-1, 61-2, and 61-3 will each be referred to as the first light source 61 when they need not be distinguished from one another, and the second light sources 62-1, 62-2, and 62-3 will each be referred to as the second light source 62 when they need not be distinguished from one another.

Although not illustrated in FIGS. 11 and 12, each of the first light source base member 51 and the second light source base member 52 has a curved shape along the surface of the finger Fg. Alternatively, one light source base member may be formed into a ring shape so as to surround the finger Fg, and the first light sources 61 and the second light sources 62 may be provided on the inner circumferential surface of the light source base member.

Figure 13:
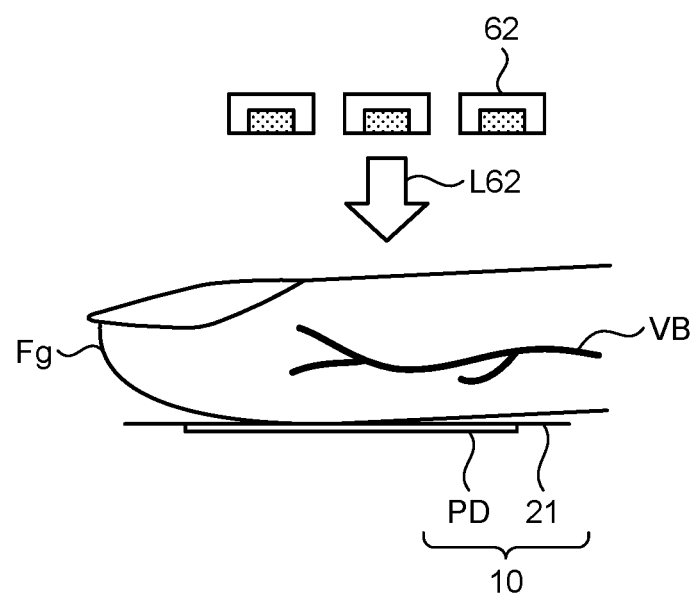
FIG. 13 is a schematic view illustrating an exemplary positional relation between the second light sources, the sensor, and a blood vessel in a finger.

FIG. 13 is a schematic view illustrating an exemplary positional relation between the second light sources 62, the sensor 10, and a blood vessel VB in the finger Fg. The second light L62 emitted from the second light sources 62 (at least one or more of second light sources 62-1, 62-2, and 62-3) is transmitted through the finger Fg and enters the photodiode PD of each of the partial detection areas PAA. At this time, the transmittance of the second light L62 through the finger Fg changes in accordance with pulsation of the blood vessel VB in the finger Fg. Therefore, the pulse rate can be calculated based on periods of the variation (amplitude) of the detection signal Vdet during a period of time longer than or equal to the pulsation period of the blood vessel VB.

In the calculation of the pulse rate based on the period of the variation (amplitude) of the detection signal Vdet, information for calculating the pulse rate can continue to be acquired more reliably by performing the calculation based on the detection signal Vdet having larger amplitude.

Figure 14:
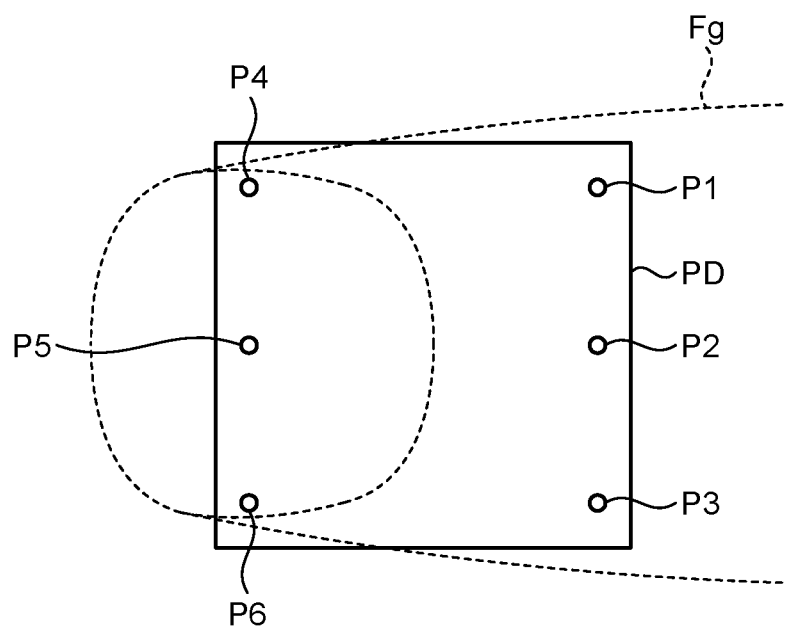
FIG. 14 is a schematic view illustrating a plurality of positions in the photodiode that are exemplarily set when a planar detection area formed by the photodiodes provided so as to face the finger is viewed in a plan view.
Figure 15:
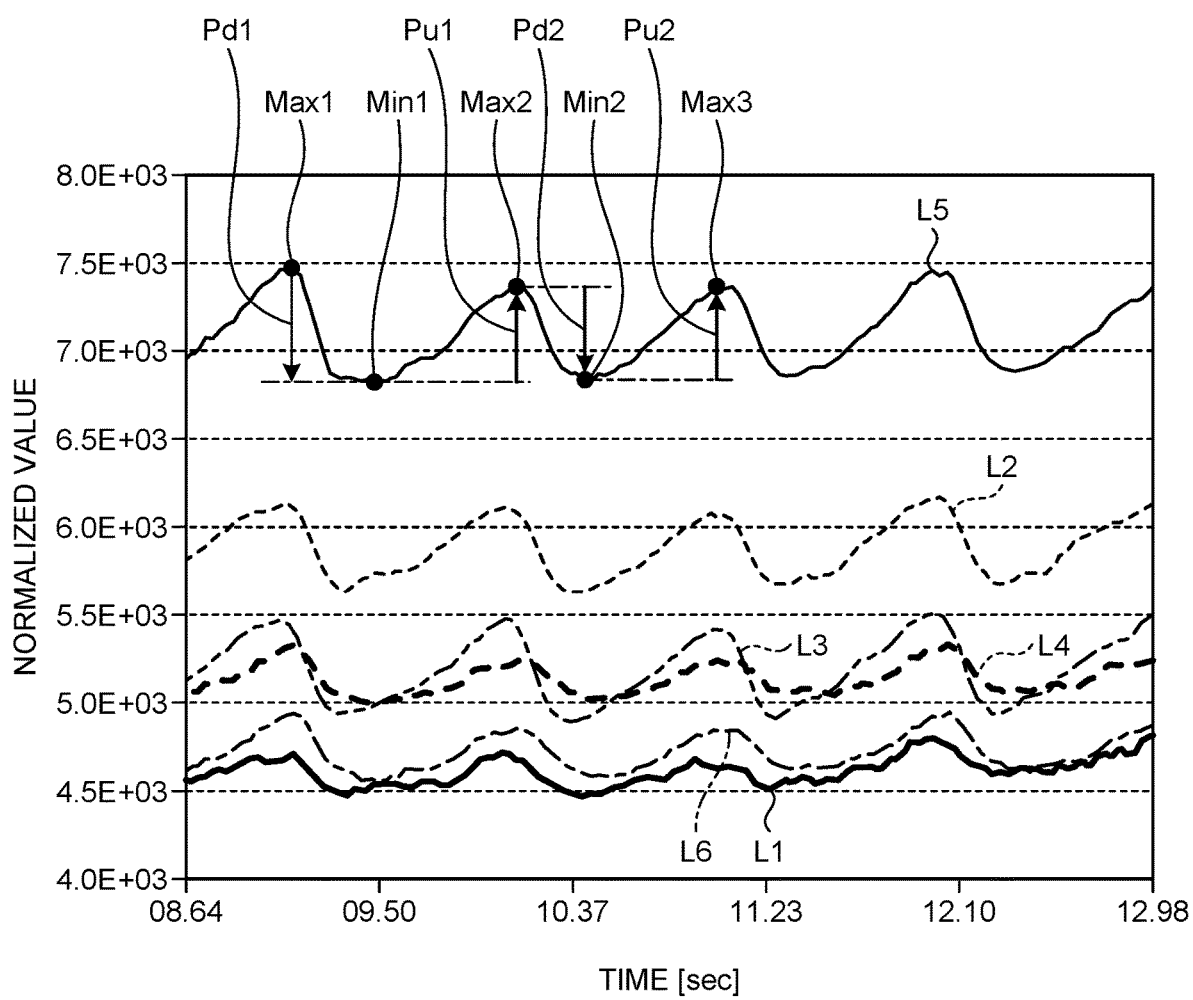
FIG. 15 is a graph illustrating temporal change examples of detection signals acquired at the positions illustrated in FIG. 14.

FIG. 14 is a schematic view illustrating a plurality of positions (positions P1, P2, P3, P4, P5, and P6) of the partial detection areas PAA in the photodiode PD that are exemplarily set when the planar detection area AA formed by the photodiodes PD provided so as to face the finger Fg is viewed in a plan view. FIG. 15 is a graph illustrating temporal change examples of the detection signals Vdet acquired at the positions illustrated in FIG. 14. A line L1 in FIG. 15 indicates a temporal change example of the detection signal Vdet from the partial detection area PAA at the position P1 of FIG. 14. A line L2 in FIG. 15 indicates a temporal change example of the detection signal Vdet from the partial detection area PAA at the position P2 of FIG. 14. A line L3 in FIG. 15 indicates a temporal change example of the detection signal Vdet from the partial detection area PAA at the position P3 of FIG. 14. A line L4 in FIG. 15 indicates a temporal change example of the detection signal Vdet from the partial detection area PAA at the position P4 of FIG. 14. A line L5 in FIG. 15 indicates a temporal change example of the detection signal Vdet from the partial detection area PAA at the position P5 of FIG. 14. A line L6 in FIG. 15 indicates a temporal change example of the detection signal Vdet from the partial detection area PAA at the position P6 of FIG. 14.

For example, the detection signal Vdet from the partial detection area PAA of the photodiode PD facing the finger Fg provided at the position P5 near the center of the tip side of the finger Fg in FIG. 14 exhibits the temporal change indicated by the line L5 in FIG. 15. Specifically, the line L5 exhibits amplitude in which rise and fall of the output of the detection signal Vdet quantified as, for example, a first peak Max1, a first bottom Min1, a second peak Max2, a second bottom Min2, a third peak Max3, . . . , alternate. The output values of the first peak Max1, the second peak Max2, and the third peak Max3 are larger than the output values of the first bottom Min1 and the second bottom Min2. Thus, a first peak-down variation Pd1 occurs from the first peak Max1 toward the first bottom Min1 on the line L5. A first peak-up variation Pu1 occurs from the first bottom Min1 toward the second peak Max2 on the line L5. A second peak-down variation Pd2 occurs from the second peak Max2 toward the second bottom Min2 on the line L5. A second peak-up variation Pu2 occurs from the second bottom Min2 toward the third peak Max3 on the line L5. In this manner, the line L5 exhibits the variation (amplitude) of the detection signal Vdet that repeats the peak-up variation and the peak-down variation, including the ranges not denoted by reference numerals in FIG. 15. Herein, a set of one peak-up variation and one peak-down variation that occur consecutively, corresponds to one pulsation that occurs in the blood vessel VB.

In the same manner as the line L5, each of the lines L1, L2, L3, L4, and L6 also exhibits the variation (amplitude) of the detection signal Vdet that repeats the peak-up variation and the peak-down variation. In this manner, each of the outputs of the detection signals Vdet from the partial detection areas PAA provided at the different positions P1, P2, P3, P4, P5, and P6 in the detection area AA exhibits the variation corresponding to the transmittance of the second light L62 that changes in accordance with the pulsation of the blood vessel VB.

As illustrated in the examples of FIG. 14 and FIG. 15, the degree of variation (amplitude) of the detection signal Vdet changes depending on the position where the partial detection area PAA faces the finger Fg. For example, the degrees of amplitude of the line L1 and the line L6 are clearly smaller than the degree of amplitude of the line L5. Thus, when the information representing the variation (amplitude) of the detection signal Vdet in accordance with the pulsation occurring in the blood vessel VB is desired to be continuously acquired more reliably, the partial detection area PAA provided at the position P5 is considered to be more preferable than the partial detection areas PAA provided at the position P1 and the position P6.

As can be seen from the difference in positional relation of the sensor 10 with the finger Fg between FIGS. 11 and 12, the sensor 10 may be positionally shifted from a living body tissue such as the finger Fg during use. When such a positional shift occurs, the degree of variation (amplitude) of the detection signal Vdet at each of the positions (for example, the positions P1, . . . , P6) provided with the partial detection areas PAA may change between preceding and following times sandwiching a predetermined time (for example, a predetermined period Pt in FIG. 16 to be explained later).

Therefore, the output processor 50 of the present embodiment performs processing (focus processing) for identifying the partial detection area PAA in which the degree of variation (amplitude) of the detection signal Vdet is larger. Specifically, the output processor 50 acquires the detection signal Vdet during the predetermined period for each of the partial detection areas PAA. The output processor 50 identifies the peak-down variation or the peak-up variation that has the largest difference between the peak and the bottom from among the peak-down variations and the peak-up variations that have been generated by the detection signals Vdet output from the partial detection areas PAA during the predetermined period. The output processor 50 identifies the partial detection area PAA that has output the detection signal Vdet that has generated the identified peak-down variation or peak-up variation.

The locations where the degree of variation (amplitude) of the detection signal Vdet is acquired are not limited to the positions P1, P2, P3, P4, P5, and P6. The output processor 50 may individually acquire the degrees of variation (amplitude) of the detection signals Vdet for all the partial detection areas PAA provided in the sensor 10 or may extract some of the partial detection areas PAA that are a plurality of the partial detection areas PAA in a sampling manner and may individually acquire the degrees of variation (amplitude) of the detection signals Vdet for the extracted partial detection areas PAA.

In the present embodiment, the output processor 50 individually acquires the degrees of variation (amplitude) of the detection signals Vdet for all the partial detection areas PAA provided in the sensor 10, performs the focus processing, and outputs data based on the detection signal Vdet from the partial detection area PAA identified by the focus processing as the pulse wave data. The pulse wave data may be data including information representing the frequency of the amplitude generated during the predetermined period, may be data including information representing a value of the pulse rate calculated by the output processor 50 based on a predefined calculation expression based on a relation between the unit time (such as a minute) of the pulse rate and the predetermined period, or may be data including information representing the change itself of the detection signal Vdet that can be drawn by, for example, the line L1.

Figure 16:
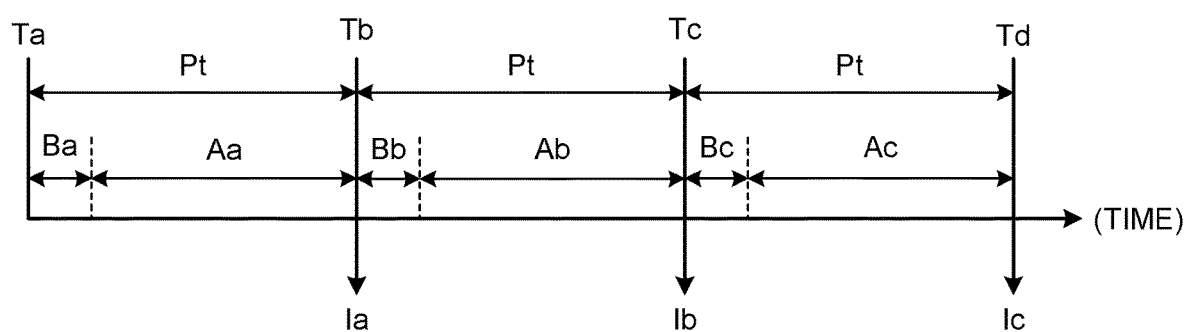
FIG. 16 is a time chart for explaining a relation between a predetermined period and an output from the photodiode identified by focus processing.

FIG. 16 is a time chart for explaining a relation between the predetermined period Pt and the output from the partial detection area PAA identified by the focus processing. In the present embodiment, the detection signal Vdet having the largest degree of variation during the predetermined period Pt from first timing Ta to second timing Tb is identified from among the detection signals Vdet acquired from the respective partial detection areas PAA during the predetermined period Pt. Data Ia based on the identified detection signal Vdet is output as the pulse wave data during the predetermined period Pt from the first timing Ta to the second timing Tb. The detection signal Vdet having the largest degree of variation during the predetermined period Pt from the second timing Tb to third timing Tc is identified from among the detection signals Vdet acquired from the respective partial detection areas PAA during the predetermined period Pt. Data Ib based on the identified detection signal Vdet is output as the pulse wave data during the predetermined period Pt from the second timing Tb to the third timing Tc. The detection signal Vdet having the largest degree of variation during the predetermined period Pt from the third timing Tc to fourth timing Td is identified from among the detection signals Vdet acquired from the respective partial detection areas PAA during a period until the predetermined period Pt. Data Ic based on the identified detection signal Vdet is output as the pulse wave data during the predetermined period Pt from the third timing Tc to the fourth timing Td. In the same manner, the pulse wave data is also output for each of the predetermined periods Pt after the fourth timing Td.

The predetermined period Pt is a period including a plurality of times of output of the detection signal Vdet during which an amplitude waveform obtained by combining the successive peak-up variation and peak-down variation is derived one or more times. The predetermined period Pt is set in advance. The predetermined period Pt is, for example, four seconds, but is not limited thereto and can be changed as appropriate.

Figure 17:
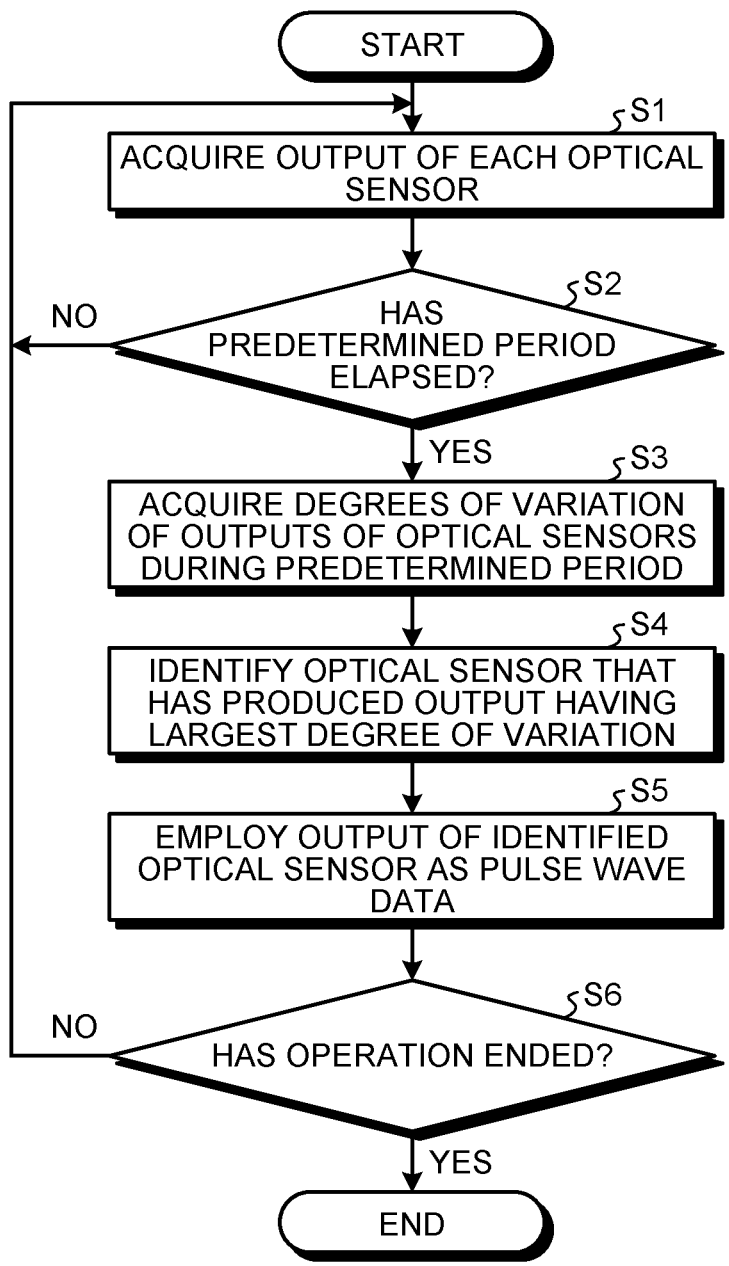
FIG. 17 is a flowchart illustrating an exemplary flow of processing for outputting pulse wave data in the first embodiment.

FIG. 17 is a flowchart illustrating an exemplary flow of processing for outputting the pulse wave data in the first embodiment. The output processor 50 acquires the output (detection signal Vdet) of each of the optical sensors (for example, the photodiodes PD) (Step S1). The output processor 50 repeats the processing at Step S1 until the predetermined period Pt elapses (No at Step S2). After the predetermined period Pt elapses (Yes at Step S2), the output processor 50 acquires the degrees of variation of the outputs (detection signals Vdet) of the respective optical sensors (photodiodes PD) (Step S3). The output processor 50 identifies an optical sensor that has the output having the largest degree of variation among the degrees of variation of the outputs (detection signals Vdet) acquired by the processing at Step S3 (Step S4). The output processor 50 employs data based on the output (detection signal Vdet) of the optical sensor identified by the processing at Step S4 as the pulse wave data (Step S5). If the operation of the detection device 1 has not ended (No at Step S6), the processing at Step S1 is performed again. If the operation of the detection device 1 has ended (Yes at Step S6), the process ends.

Although the above has described the acquisition of the pulse wave data based on the detection signal Vdet having the largest degree of variation, the detection signal Vdet having the highest peak value among the peak values (Max1, Max2, Max3, . . . ) may be employed instead of the detection signal Vdet having the largest degree of variation. That is, the pulse wave data may be acquired based on the detection signal Vdet having the highest peak value.

As described above, according to the first embodiment, the detection device 1 includes the optical sensors (for example, the photodiodes PD) arranged in the detection area AA, the light sources (for example, the first light sources 61 and the second light sources 62) configured to emit light that is emitted to the object to be detected (for example, the finger Fg) and is detected by the optical sensors, and the processor (for example, the output processor 50) that performs the processing based on the outputs from the optical sensors. The processor determines the optical sensor the output of which is to be employed from among the optical sensors, based on the outputs of the respective optical sensors obtained at a cycle of a predetermined period (for example, the predetermined period Pt). With this configuration, even if the positional relation between the optical sensors and the object to be detected changes, the optical sensor the output of which is to be employed is appropriately determined at the cycle of the predetermined period. Therefore, the output in response to the change in the position can be obtained at the cycle of the predetermined period. Consequently, it is possible to deal with the change in the positional relation between the optical sensors and the object to be detected.

The processor (for example, the output processor 50) employs the output of the optical sensor (for example, the photodiode PD) that has produced the largest output during the predetermined period (for example, the predetermined period Pt), or that has produced the output having the largest degree of variation during the predetermined period. This processing employs the output of the optical sensor that has produced the largest output during the predetermined period or that has produced the output having the largest degree of variation during the predetermined period as the most appropriate output for obtaining the sensor output Vo including the pulse wave data. As a result, the accuracy of the pulse wave data can be further improved even if the positional relation between the optical sensors and the object to be detected changes. Consequently, it is possible to deal with the change in the positional relation between the optical sensors and the object to be detected.

Second Embodiment

The following describes a second embodiment. With regard to the description of the second embodiment, the same components as those of the first embodiment will be denoted by the same reference numerals and will not be described.

In the first embodiment, the optical sensor (photodiode PD) that has the output (detection signal Vdet) having the largest degree of variation is identified, and the data based on the output from the optical sensor is employed as the pulse wave data. The pulse wave data of the second embodiment differs from that of the first embodiment in that the data is based on an output from the group area (group area PAG) including the optical sensor (photodiode PD) that has the output (detection signal Vdet) having the largest degree of variation.

Figure 18:
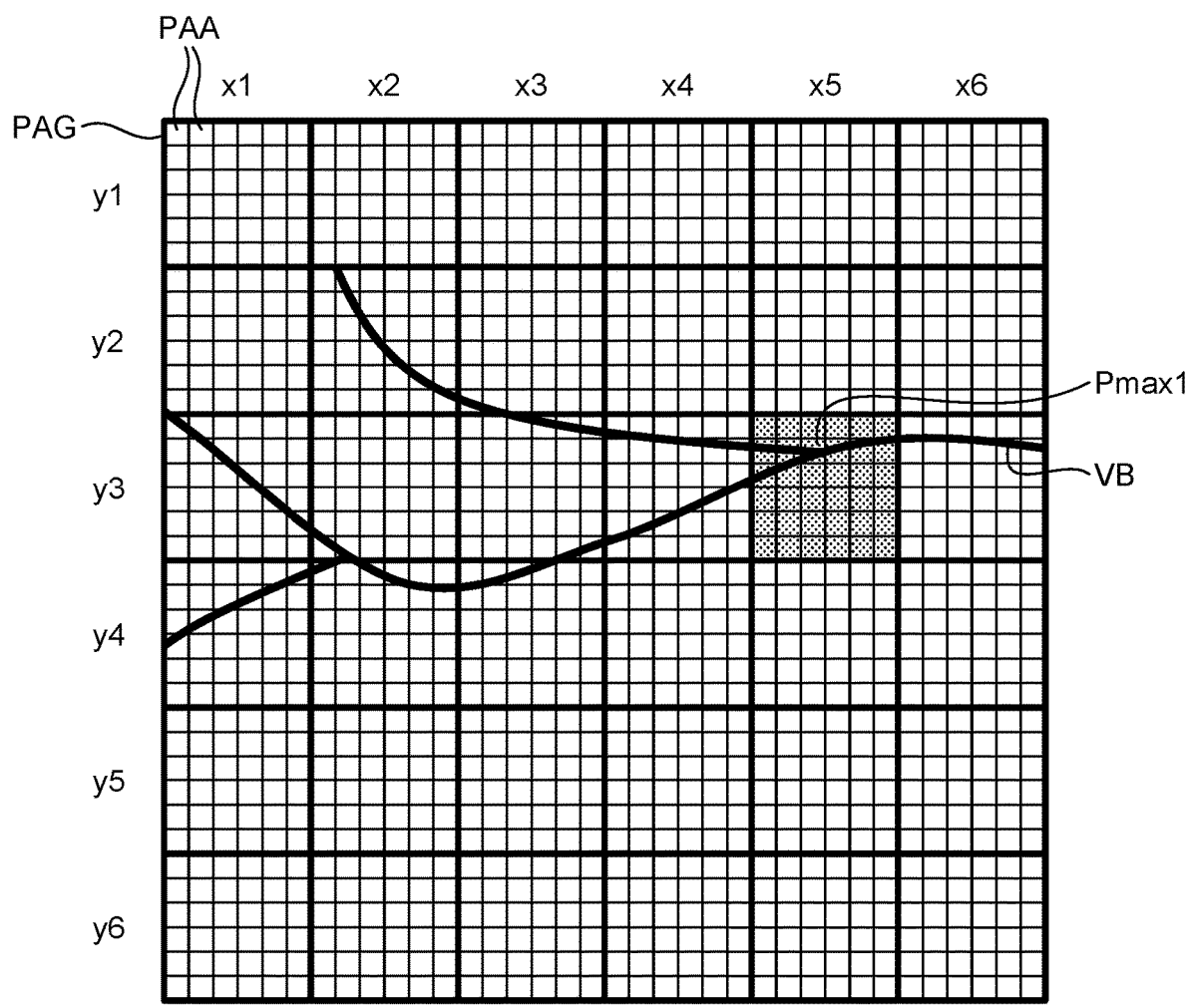
FIG. 18 is a schematic diagram for explaining pulse wave data acquisition control on a group area basis.
Figure 19:
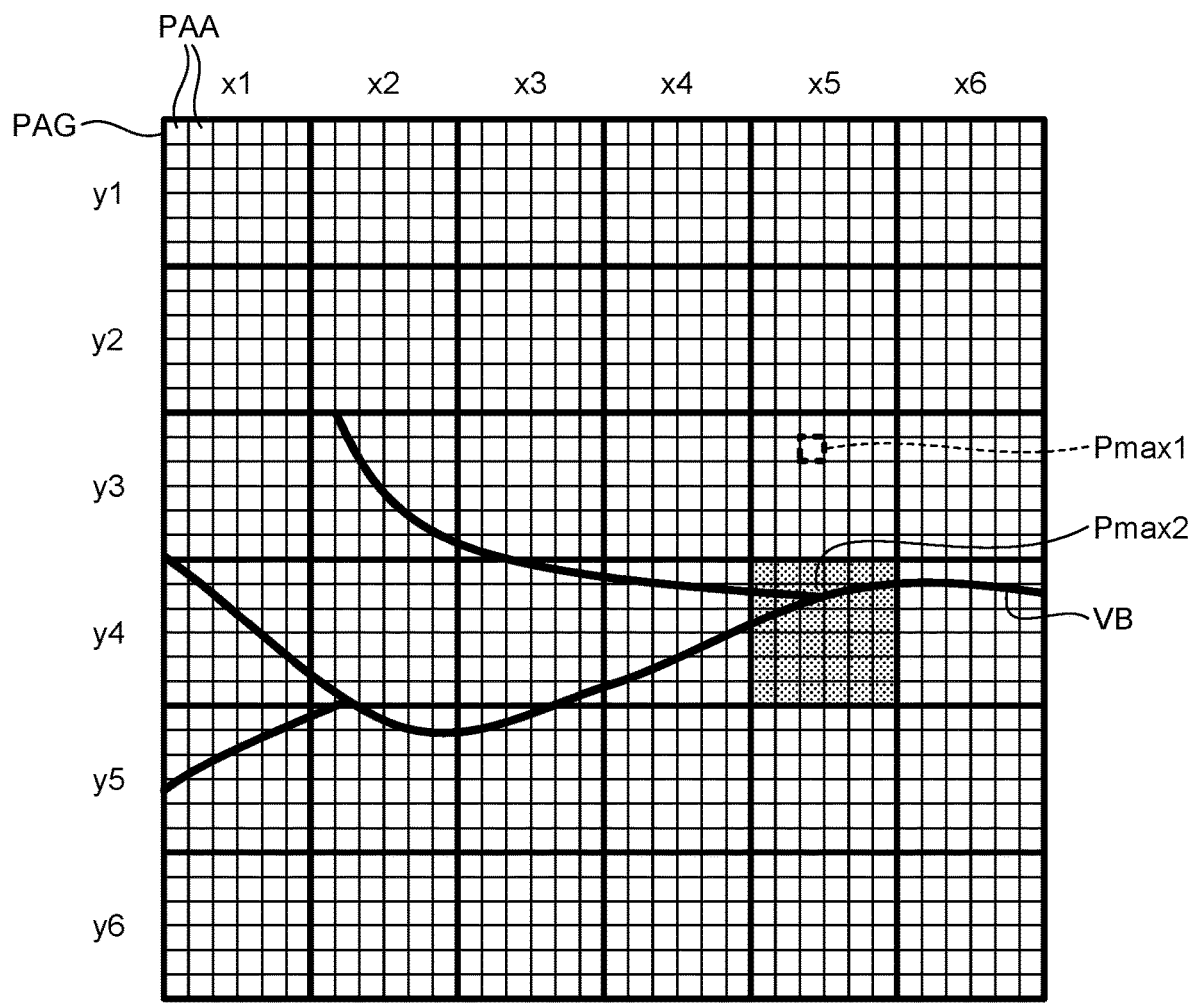
FIG. 19 is another schematic diagram for explaining the pulse wave data acquisition control on a group area basis.

FIGS. 18 and 19 are schematic diagrams for explaining pulse wave data acquisition control on a group area PAG basis. Although FIGS. 18 and 19 are schematic diagrams obtained by enlarging, for example, the position P5 of FIG. 14 and the vicinity of the position P5, the present embodiment is not limited to these diagrams. FIGS. 18 and 19 exemplarily illustrate a detection area of the sensor 10 in which x×y=6×6 of the group areas PAG are arranged in a matrix having a row-column configuration. To distinguish the positions of x×y=6×6 of the group areas PAG, coordinates x1, x2, x3, x4, x5, and x6 are assigned in the first direction Dx, and coordinates y1, y2, y3, y4, y5, and y6 are assigned in the second direction Dy. For example, the group area PAG at (x1,y1) refers to the group area PAG corresponding to a position represented by combining the coordinate x1 with the coordinate y1. In FIGS. 18 and 19, a predetermined number (for example, x×y=6×6) of the partial detection areas PAA arranged in a matrix having a row-column configuration are exemplarily defined collectively as one group areas PAG.

FIG. 18 illustrates an example in which the blood vessel VB is located in a region of the coordinates y2, y3, and y4. Among the partial detection areas PAA illustrated in FIG. 18, the partial detection area PAA that produces the output (detection signal Vdet) having the largest degree of variation is assumed to be located in a position Pmax1 in the group area PAG at (x5,y3).

FIG. 19 illustrates an example in which the blood vessel VB is located in a region of the coordinates y3, y4, and y5. The difference between FIGS. 18 and 19, that is, the difference between the positions of the blood vessel VB is caused by, for example, the positional shift of the sensor 10 with respect to the finger Fg (refer to FIGS. 11 and 12). When the positional shift occurs from the state of FIG. 18 to the state of FIG. 19, the position of the partial detection area PAA that produces the output (detection signal Vdet) having the largest degree of variation is displaced from the position Pmax1 to a position Pmax2 in the group area PAG at (x5,y4).

In the first embodiment, the output (detection signal Vdet) from the partial detection area PAA in the position Pmax1 is employed as the output during the predetermined period Pt before the positional shift (refer to FIG. 18), and the output (detection signal Vdet) from the partial detection area PAA in the position Pmax2 is employed as the output during the predetermined period Pt after the positional shift (refer to FIG. 19). In contrast, in the second embodiment, the outputs (detection signals Vdet) from the partial detection areas PAA provided in the group area PAG at (x5,y3) including the partial detection area PAA in the position Pmax1 are employed as outputs during the predetermined period Pt before the positional shift (refer to FIG. 18), and the outputs (detection signals Vdet) from the partial detection areas PAA provided in the group area PAG at (x5,y4) including the partial detection area PAA in the position Pmax2 are employed as outputs during the predetermined period Pt after the positional shift (refer to FIG. 19). In this manner, in the second embodiment, the outputs from the group area PAG including the partial detection area PAA that produces the output (detection signal Vdet) having the largest degree of variation are employed.

Figure 20:
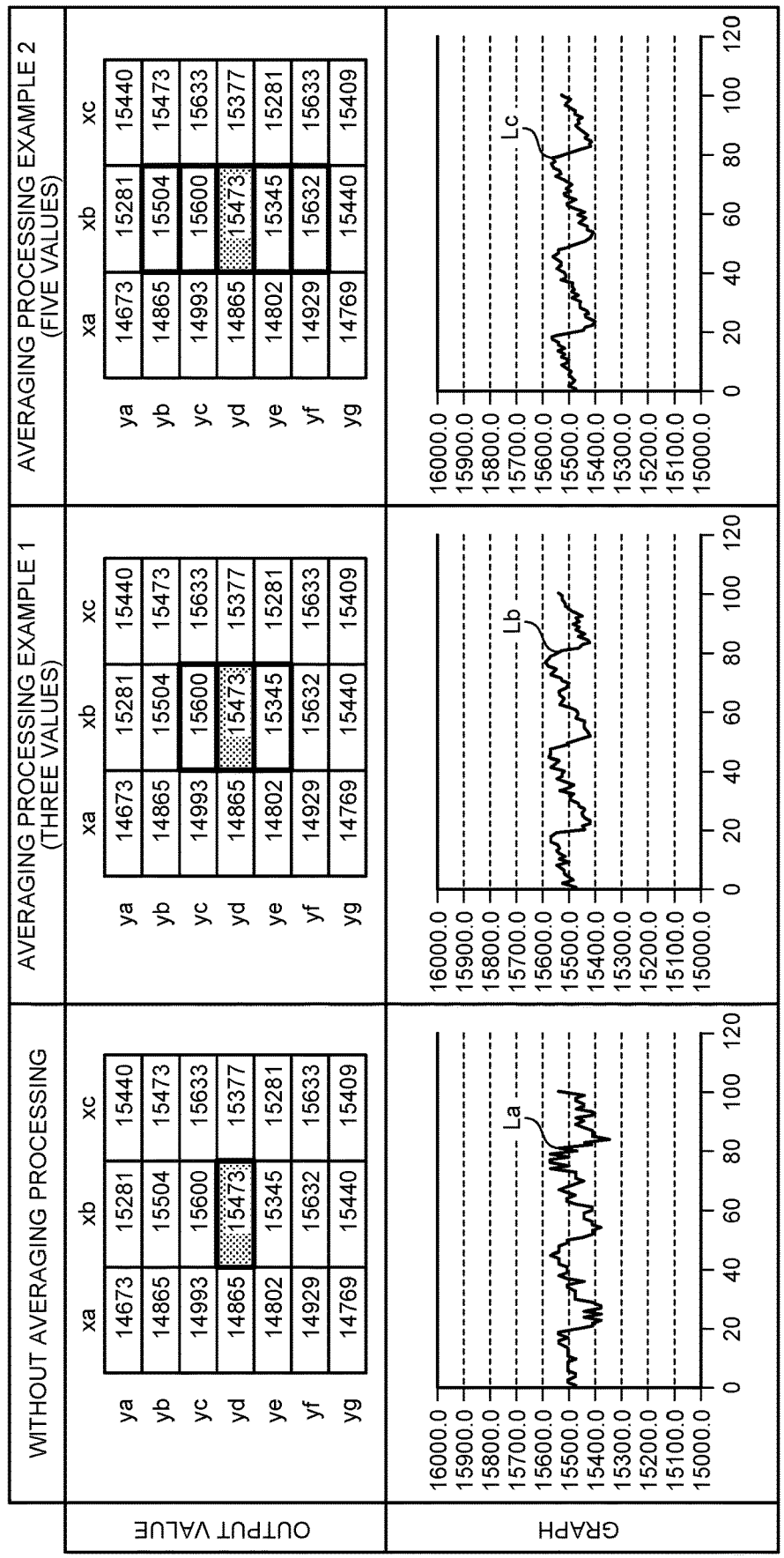
FIG. 20 is an explanatory diagram illustrating examples of averaging processing of outputs from the partial detection areas.

FIG. 20 is an explanatory diagram illustrating examples of averaging processing of the outputs from the partial detection areas PAA. In the second embodiment, when the outputs (detection signals Vdet) from the partial detection areas PAA provided in the group area PAG including the partial detection area PAA that produces the output (detection signal Vdet) having the largest degree of variation are employed, the averaging processing is performed to average the outputs from the partial detection areas PAA. In the averaging processing, the outputs (detection signals Vdet) of the respective partial detection areas PAA are quantified using analog-to-digital conversion processing to obtain output values, the output values of the partial detection areas PAA are added together, and the sum of the output values is divided by the number of the partial detection areas PAA the output values of which have been added together.

In FIG. 20, the "output value" row of the tables indicates the output values obtained by quantifying the outputs (detection signals Vdet) from the respective partial detection areas PAA. In each of the tables, in order to distinguish the position of each of the partial detection areas PAA, coordinates xa, xb, and xc are assigned in the first direction Dx, and coordinates ya, yb, yc, yd, ye, yf, and yg are assigned in the second direction Dy. That is, the value in one cell of the table indicates the output value of one of the partial detection areas PAA. The value in each cell is merely exemplary, and does not indicate that the output value from each of the partial detection areas PAA is limited to the value in the cell.

The values in the cells of the "output value" row are the same among the "without averaging processing" column, the "AVERAGING PROCESSING EXAMPLE 1 (THREE VALUES)" column, and the "AVERAGING PROCESSING EXAMPLE 2 (FIVE VALUES)" column in FIG. 20. While the output value indicated in each cell of the tables is an output value at certain timing, graphs of the output values illustrated in the "graph" row are graphs each indicating how the output value, which has been obtained a plurality of times during a period (for example, the predetermined period Pt) including the certain timing, has changed during the period.

A line La in the graph "without averaging processing" of FIG. 20 indicates the temporal change of the output value of each of the partial detection areas PAA when the output value is employed as it is. A line Lb in the graph "AVERAGING PROCESSING EXAMPLE 1 (THREE VALUES)" employs the average value of the output values of three of the partial detection areas PAA continuously arranged in one direction (for example, the second direction Dy). As illustrated in the graph "AVERAGING PROCESSING EXAMPLE 1 (THREE VALUES)", performing the averaging processing reduces the influence of noise on the output values, and thus, further clarifies the periodicity of peaks and bottoms indicated by the temporal change of the output values. A line Lc in the graph "AVERAGING PROCESSING EXAMPLE 2 (FIVE VALUES)" employs the average value of the output values of five of the partial detection areas PAA continuously arranged in the one direction. By increasing the number of the partial detection areas PAA having the output values to be averaged, the influence of various types of noise, such as device variations and power supply noise, in the output values is further reduced, and thus, the periodicity of peaks and bottoms indicated by the temporal change of the output values is further clarified.

In FIG. 20, the number (predetermined number) of the partial detection areas PAA having the output values to be averaged is merely an example for explaining the averaging processing. The present embodiment is not limited to this example. In the second embodiment, for example, the output values of the partial detection areas PAA provided in one of the group areas PAG including the partial detection area PAA that produces the output (detection signal Vdet) having the largest degree of variation are averaged, and the averaged value is employed as the output value from the group area PAG. In the second embodiment, the output values of the partial detection areas PAA provided in the one of the group areas PAG and the output values of the partial detection areas PAA provided in a group area PAG near the one of the group areas PAG may be averaged, and the averaged value may be employed as the output value from the group area PAG. The group area PAG near the one of the group areas PAG may be, for example, a group area PAG adjacent to the one of the group areas PAG along the first direction Dx or the second direction Dy, or may be a plurality of group areas PAG arranged continuously to the one of the group areas PAG along either the first direction Dx or the second direction Dy.

Figure 21:
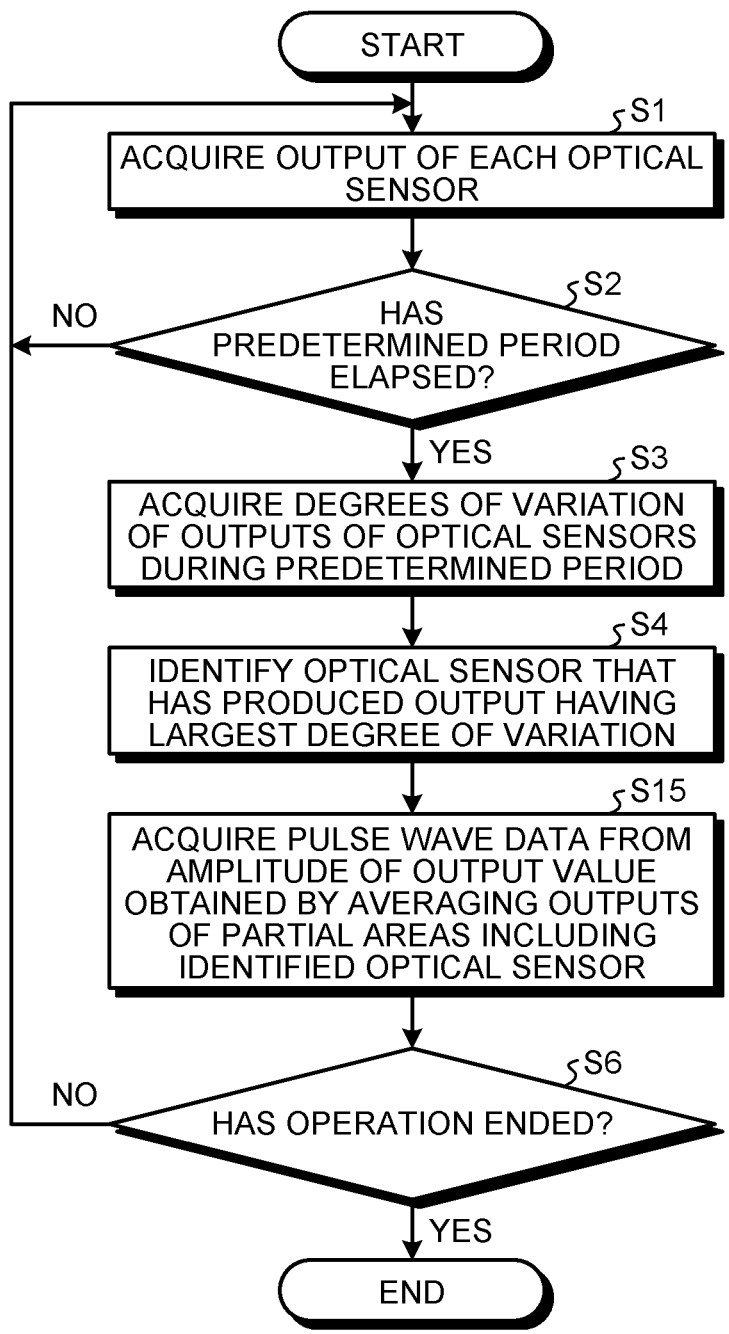
FIG. 21 is a flowchart illustrating an exemplary flow of processing for outputting the pulse wave data in a second embodiment.

FIG. 21 is a flowchart illustrating an exemplary flow of processing for outputting the pulse wave data in the second embodiment. The flow of the processing of the second embodiment illustrated in FIG. 21 is the same as that of the processing of the first embodiment except that the processing at Step S5 in the flow of the processing of the first embodiment illustrated in FIG. 17 is replaced with processing at Step S15.

The output processor 50 performs, as the processing at Step S15, the averaging processing to average the outputs of the group areas (group areas PAG) including the optical sensor (photodiode PD of the partial detection area PAA) identified by the processing at Step S4, and acquires the pulse wave data based on the amplitude indicated by the temporal change of the output value obtained by the averaging processing.

As described above, the second embodiment is the same as the first embodiment except in the respects otherwise explained.

According to the second embodiment, the detection area AA includes a plurality of group areas (for example, the group areas PAG). Each of the group areas includes a plurality of optical sensors (for example, the photodiodes PD). The output processor 50 employs the output of the group area that includes the optical sensor that has produced the largest output during the predetermined period (for example, the predetermined period Pt), or that has produced the output having the largest degree of variation during the predetermined period. This processing employs the output of the group area that includes the optical sensor that has produced the largest output during the predetermined period or that has produced the output having the largest degree of variation during the predetermined period as the most appropriate output for obtaining the sensor output Vo including the pulse wave data. As a result, the accuracy of the pulse wave data can be further improved even if the positional relation between the optical sensors and the object to be detected changes. Thus, it is possible to deal with the change in the positional relation between the optical sensors and the object to be detected.

The optical sensors (for example, the photodiodes PD) are arranged in a matrix having a row-column configuration in the detection area AA. The output processor 50 performs the averaging processing to average the outputs of a predetermined number of the optical sensors that are two or more adjacent optical sensors and are not all the optical sensors, and determines, based on the output averaged by the averaging processing, the optical sensor the output of which is to be employed. This operation further reduces the influence of the various types of noise in the output values, and thus, further clarifies the periodicity of peaks and bottoms indicated by the temporal change of the output values. Thus, the accuracy of the sensor output Vo such as the pulse wave data can be further improved. The specific content of the averaging processing is not limited to this processing, and can be changed as appropriate. For example, at least one of the gate lines GCL and a plurality of the signal lines SGL, or a plurality of the gate lines GCL and at least one of the signal lines SGL may be handled collectively, and the outputs from the adjacent partial detection areas PAA may be simultaneously read.

Third Embodiment

The following describes a third embodiment. With regard to the description of the third embodiment, the same components as those of the first embodiment or the second embodiment will be denoted by the same reference numerals and will not be described.

In the third embodiment, a fingerprint detection is performed by generating the fingerprint pattern of a finger Fg as described with reference to FIGS. 11 and 12. The fingerprint detection is performed at intervals of the predetermined period Pt. The output processor 50 calculates an amount of positional shift of the photodiode PD with respect to the finger Fg based on a difference in the positional relation between the position of the fingerprint pattern detected first (initial fingerprint pattern) and the position of the fingerprint pattern detected thereafter. The output processor 50 corrects the positional shift of the optical sensor (partial detection area PAA) to be handled as an output to be employed, based on the calculated amount of shift.

As a specific method for detecting the fingerprint, both of the following methods can be used: a method in which a fingerprint pattern is generated using the sensor 10 as an optical sensor based on the detection of the light from at least either the first light sources 61 or the second light sources 62, and a method in which the asperities of the fingerprint are recognized by a capacitive sensor using the capacitance of the capacitive element Ca.

In the third embodiment, as an example, the first light L61 has a wavelength from 360 nm to 800 nm, for example, at approximately 500 nm, and the second light L62 has a wavelength from 800 nm to 930 nm, for example, at approximately 850 nm. That is, the wavelength of the second light L62 is longer than the wavelength of the first light L61. In this case, the first light L61 is visible light, and the second light L62 is infrared light.

When light having one of the two wavelengths of the first light L61 and the second light L62 is used to detect a fingerprint, and light having the other of the two wavelengths is used to detect a blood vessel and a pulse wave pattern, the first light L61 is used for detecting the fingerprint, and the second light L62 is used for detecting the blood vessel and pulse wave pattern. Light having one wavelength of the second light L62 may be used to detect both the fingerprint and the blood vessel.

Figure 22:
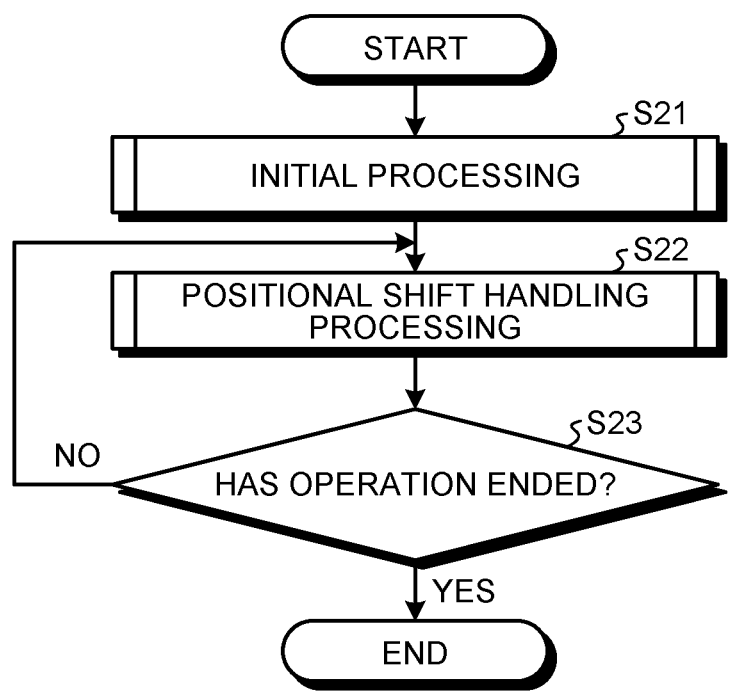
FIG. 22 is a flowchart illustrating an exemplary flow of processing for outputting the pulse wave data in a third embodiment and a fourth embodiment.

FIG. 22 is a flowchart illustrating an exemplary flow of processing for outputting the pulse wave data in the third embodiment and a fourth embodiment (to be described later). In the third embodiment and the fourth embodiment (to be described later), initial processing is first performed (Step S21). Then, positional shift handling processing is performed (Step S22). The processing at Step S22 is repeated until the operation of the detection device 1 ends (No at Step S23). After the operation of the detection device 1 ends (Yes at Step S23), the process ends.

Figure 23:
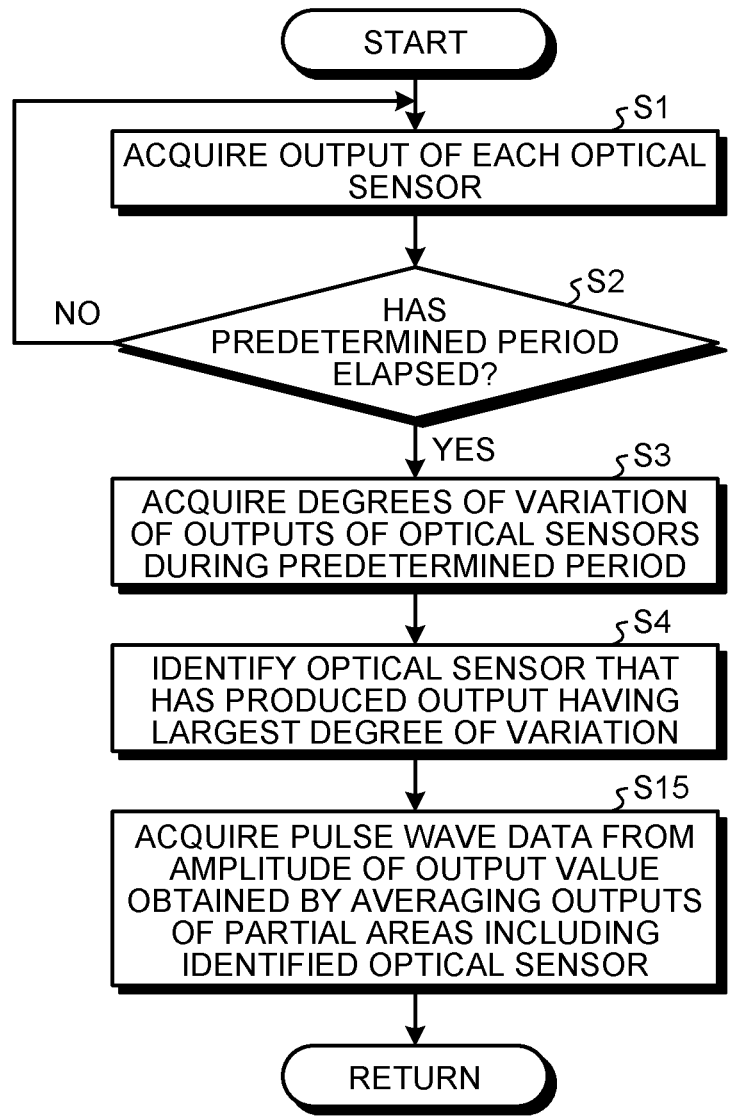
FIG. 23 is a flowchart illustrating an exemplary flow of initial processing of FIG. 22.

FIG. 23 is a flowchart illustrating an exemplary flow of the initial processing of FIG. 22. The initial processing is the same as the processing described with reference to the flowchart illustrated in FIG. 21 except that the processing at Step S6 of the flowchart illustrated in FIG. 21 is omitted. The return after the processing at Step S15 of FIG. 23 indicates that the processing (initial processing) at Step S21 illustrated in FIG. 22 ends, and the processing (positional shift handling processing) at Step S22 as the next processing is performed.

Figure 24:
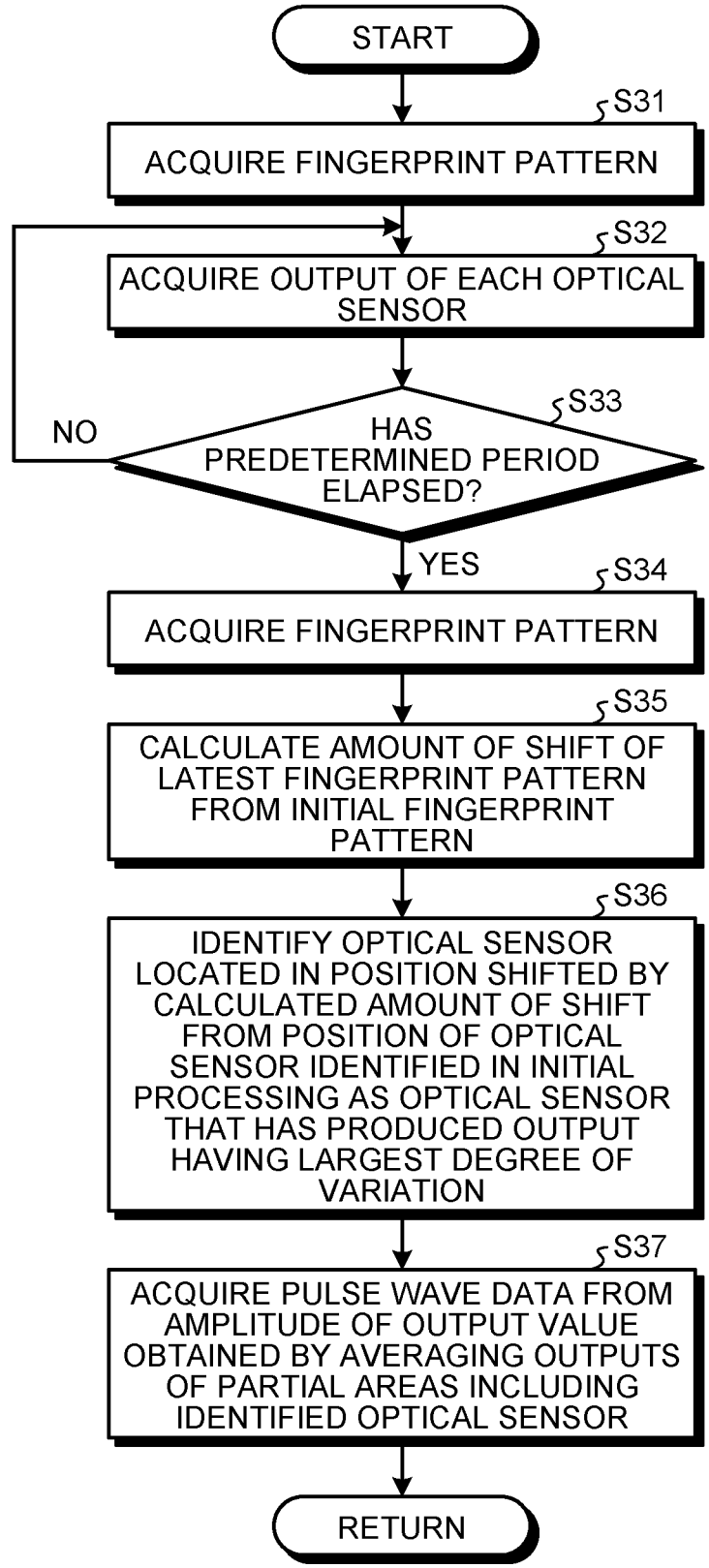
FIG. 24 is a flowchart illustrating an exemplary flow of positional shift handling processing of FIG. 22 in the third embodiment.

FIG. 24 is a flowchart illustrating an exemplary flow of the positional shift handling processing of FIG. 22 in the third embodiment. The fingerprint pattern is first acquired (Step S31). The acquisition of the fingerprint pattern at Step S31 is performed based on, for example, the output of each of the optical sensors (photodiodes PD) during the initial processing. Although the fingerprint pattern is generated based on the output at any timing during the initial processing, the timing is set in advance (for example, the initial time).

The output processor 50 acquires the output (detection signal Vdet) of each of the optical sensors (photodiodes PD) (Step S32). The output processor 50 repeats the processing at Step S32 until the predetermined period Pt elapses (No at Step S33). After the predetermined period Pt elapses (Yes at Step S33), the fingerprint pattern is acquired (Step S34). The acquisition of the fingerprint pattern at Step S34 is performed based on, for example, the latest output of each of the optical sensors (photodiodes PD). However, the output is not limited thereto and only needs to be the output of each of the optical sensors (photodiodes PD) within a period that starts before not longer than the predetermined period Pt.

The output processor 50 calculates the amount of shift of the latest fingerprint pattern from the initial fingerprint pattern (Step S35). Specifically, the output processor 50 compares, as the processing at Step S35, the positional relation between the fingerprint pattern acquired by the processing at Step S31 and the partial detection areas PAA with the positional relation between the fingerprint pattern acquired by the processing at Step S34 and the partial detection areas PAA. The output processor 50 determines whether the position of the partial detection areas PAA in which the asperities determined to be the same fingerprint pattern were detected has shifted, based on collation processing such as detection of feature points included in the fingerprint pattern. If the position has shifted, the output processor 50 quantifies the amount of the shift as amounts of shifts of the partial detection areas PAA in the first direction Dx and the second direction Dy.

The output processor 50 identifies the optical sensor (photodiode PD) located in the position shifted by the amount of shift calculated by the processing at Step S35 from the position of the optical sensor identified by the processing at Step S4 in the initial processing as the optical sensor (photodiode PD) that has the output having the largest degree of variation (Step S36). The output processor 50 acquires the pulse wave data from the amplitude of the output value obtained by averaging the outputs of the group area (group area PAG) including the optical sensor identified by the processing at Step S36 (Step S37). The processing at Step S37 is the same as the processing at Step S15 except that the reference for determining the group area is changed from the optical sensor identified by the processing at Step S4 to the optical sensor identified by the processing at Step S36. The return after the processing at Step S37 of FIG. 24 and FIG. 26 to be explained later indicates that the processing (positional shift handling processing) at Step S22 illustrated in FIG. 22 ends, and the processing at Step S23 as the next processing is performed.

In the description with reference to FIGS. 22, 23, and 24, the fingerprint detection is performed at the time of pulse wave measurement, that is, at every interval of the predetermined period Pt in which the variation (amplitude) of the output for acquiring the pulse wave occurs. However, the present embodiment is not limited thereto. The fingerprint detection may be performed during a full operation period (to be described later), and not performed in the other period, so that the fingerprint detection is performed once for a plurality of times of pulse wave measurement (skipped fingerprint measurement). As described above, the third embodiment is the same as the second embodiment except in the respects otherwise explained.

According to the third embodiment, the detection area AA faces the finger Fg (refer to FIGS. 11 and 12). The output processor 50 determines, based on the fingerprint pattern generated based on the output of each of the partial detection areas PAA, the optical sensor the output of which is to be employed from among the optical sensors (for example, the photodiodes PD). With this configuration, even if the positional relation between the optical sensors and the finger Fg changes, the output to be employed is determined based on the positional shift of the detected fingerprint pattern. Therefore, the output in response to the change in the position can be obtained at the cycle of the predetermined period. Thus, it is possible to deal with the change in the positional relation between the optical sensors and the finger Fg.

Modification of Third Embodiment

The following describes a modification in which the processing from Step S35 to Step S37 in the third embodiment is replaced with other processing. Specifically, in the modification, the process branches based on whether the latest fingerprint pattern (refer to Step S34) has shifted from the initial fingerprint pattern (refer to Step S31).

Figure 25:
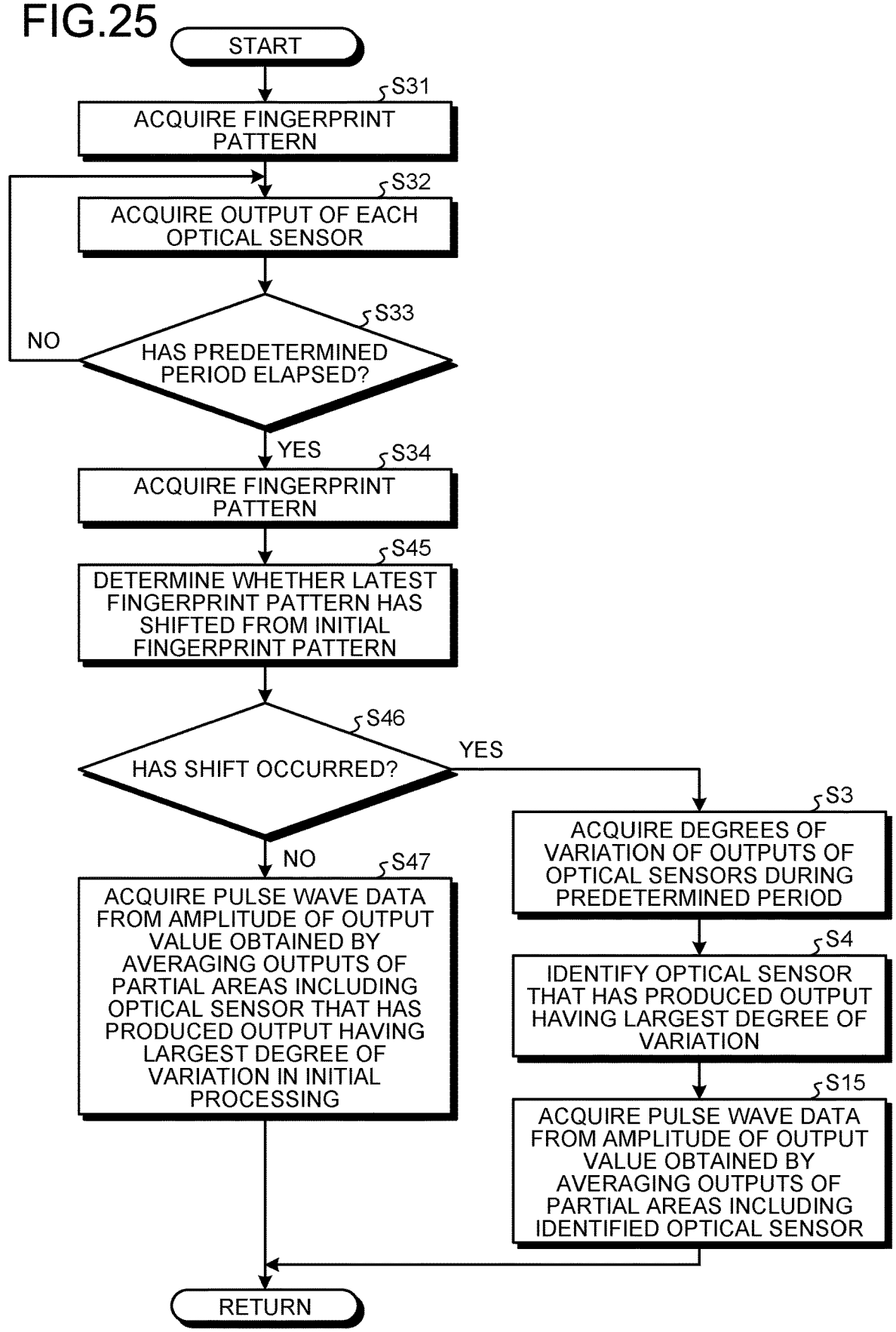
FIG. 25 is a flowchart illustrating an exemplary flow of the positional shift handling processing of FIG. 22 in a modification of the third embodiment.

FIG. 25 is a flowchart illustrating an exemplary flow of the positional shift handling processing of FIG. 22 in the modification of the third embodiment. The processing from Step S31 to Step S34 is the same as the processing described with reference to FIG. 24.

The output processor 50 determines whether the latest fingerprint pattern has shifted from the initial fingerprint pattern (Step S45). Specifically, the output processor 50 compares, as the processing at Step S45, the positional relation between the fingerprint pattern acquired by the processing at Step S31 and the partial detection areas PAA with the positional relation between the fingerprint pattern acquired by the processing at Step S34 and the partial detection areas PAA. The output processor 50 determines whether the position of the partial detection areas PAA in which the asperities determined to be the same fingerprint pattern were detected has shifted, based on the collation processing such as the detection of the feature points included in the fingerprint pattern.

If the processing at Step S45 determines that the shift has occurred (Yes at Step S46), the output processor 50 sequentially performs the processing at Step S3, the processing at Step S4, and the processing at Step S15. If, in contrast, the processing at Step S45 determines that the shift has not occurred (No at Step S46), the output processor 50 acquires the pulse wave data from the amplitude of the output value obtained by averaging the outputs of the group area (group area PAG) including the optical sensor (photodiode PD) that is determined to have produced the output having the largest degree of variation by the processing at Step S4 in the initial processing (Step S47). The return after the processing at Step S15 of FIG. 25 and FIG. 27 to be explained later and after the processing at Step S47 indicates that the processing (positional shift handling processing) at Step S22 illustrated in FIG. 22 ends, and the processing at Step S23 as the next processing is performed.

As described above, the modification of the third embodiment is the same as the third embodiment except in the respects otherwise explained.

Fourth Embodiment

The following describes the fourth embodiment. With regard to the description of the fourth embodiment, the same components as those of the first embodiment, the second embodiment, and the third embodiment will be denoted by the same reference numerals and will not be described.

In the third embodiment, the fingerprint pattern is used in the positional shift handling processing. The fourth embodiment differs from the third embodiment in that the vascular pattern generated based on the shape of the blood vessel VB facing the detection area AA is used in the positional shift handling processing. Specifically, in the fourth embodiment, the initial processing in the flow of processing described with reference to FIG. 22 is the same as that of the third embodiment, and the positional shift handling processing partially differs from that of the third embodiment.

Figure 26:
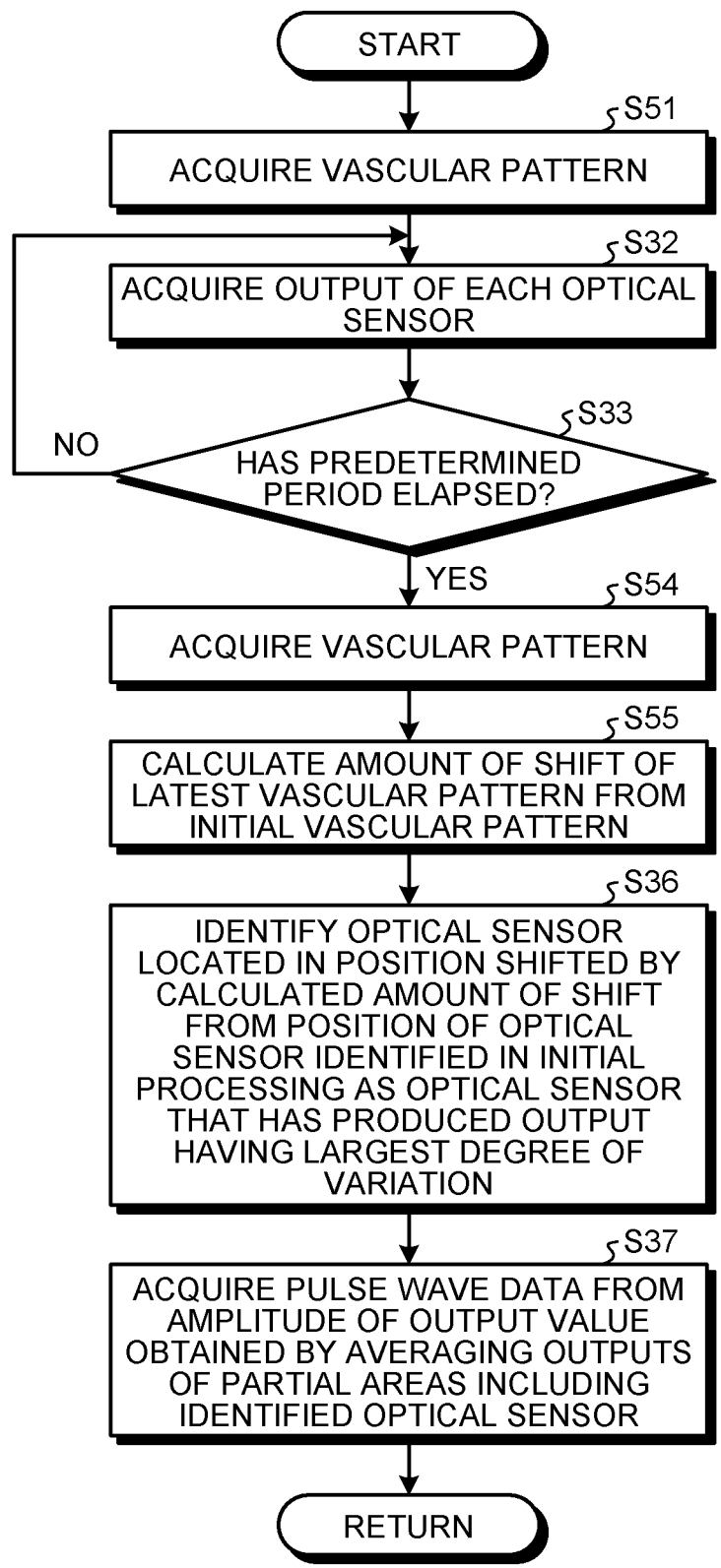
FIG. 26 is a flowchart illustrating an exemplary flow of the positional shift handling processing of FIG. 22 in the fourth embodiment.

FIG. 26 is a flowchart illustrating an exemplary flow of the positional shift handling processing of FIG. 22 in the fourth embodiment. In the fourth embodiment, the acquisition of the vascular pattern is performed as processing at Step S51 instead of the processing at Step S31 in the third embodiment. The acquisition of the vascular pattern at Step S51 is performed based on, for example, the output of each of the optical sensors (photodiodes PD) during the initial processing. Although the vascular pattern is generated based on the output at any timing during the initial processing, the timing is set in advance (for example, the initial time).

In the fourth embodiment, the acquisition of the vascular pattern is performed as processing at Step S54 instead of the processing at Step S34 in the third embodiment. The acquisition of the vascular pattern at Step S54 is performed based on, for example, the latest output of each of the optical sensors (photodiodes PD). However, the output is not limited thereto and only needs to be the output of each of the optical sensors (photodiodes PD) within a period that starts before not longer than the predetermined period Pt.

In the fourth embodiment, processing at Step S55 is performed instead of the processing at Step S35 in the third embodiment. In the processing at Step S55, the output processor 50 calculates the amount of shift of the latest vascular pattern from the initial vascular pattern. Specifically, the output processor 50 compares the positional relation between the vascular pattern acquired by the processing at Step S51 and the partial detection areas PAA with the positional relation between the vascular pattern acquired by the processing at Step S54 and the partial detection areas PAA. The output processor 50 performs processing to determine whether the position of the partial detection areas PAA in which the same vascular pattern was detected has shifted, based on the collation processing such as the detection of feature points included in the vascular pattern. If the position has shifted, the output processor 50 quantifies the amount of the shift as amounts of shifts of the partial detection areas PAA in the first direction Dx and the second direction Dy.

As described above, the fourth embodiment is the same as the third embodiment except in the respects otherwise explained. In the fourth embodiment, the vascular pattern corresponding to the blood vessel VB is employed. The type of the blood vessel VB may be any blood vessel, such as an artery, a vein, or other.

According to the fourth embodiment, the detection area AA faces the living body tissue (for example, the finger Fg or a wrist Wr, which will be described later) including therein a blood vessel (for example, the blood vessel VB). The output processor 50 determines the optical sensor the output of which is to be employed from among the optical sensors, based on the vascular pattern (for example, the pattern of the blood vessel VB) generated based on the outputs of the respective optical sensors (for example, the photodiodes PD). With this configuration, even if the positional relation between the optical sensors and the living body tissue changes, the output to be employed is determined based on the positional shift of the detected vascular pattern. Therefore, the output in response to the change in the position can be obtained at the cycle of the predetermined period. Thus, it is possible to deal with the change in the positional relation between the optical sensors and the living body tissue.

Modification of Fourth Embodiment

The following describes a modification in which the processing at Step S55, Step S36, and Step S37 in the fourth embodiment is replaced with other processing. Specifically, in the same manner as the replacement of the fingerprint pattern in the third embodiment with the vascular pattern in the fourth embodiment, the fingerprint pattern in the modification of the third embodiment is replaced with the vascular pattern in the modification of the fourth embodiment. That is, in the modification of the fourth embodiment, the process branches based on whether the latest vascular pattern (refer to Step S54) has shifted from the initial vascular pattern (refer to Step S51).

Figure 27:
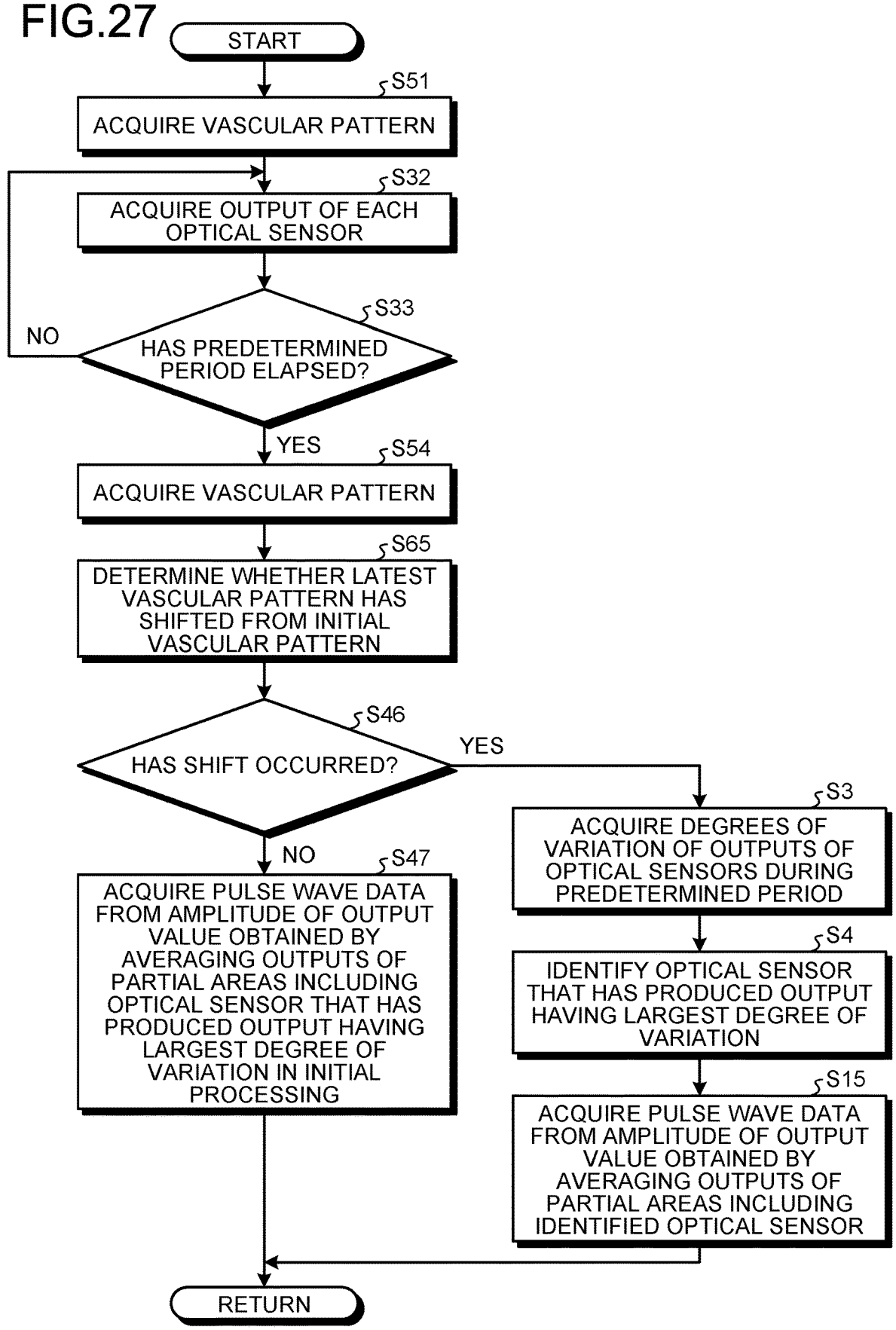
FIG. 27 is a flowchart illustrating an exemplary flow of the positional shift handling processing of FIG. 22 in a modification of the fourth embodiment.

FIG. 27 is a flowchart illustrating an exemplary flow of the positional shift handling processing of FIG. 22 in the modification of the fourth embodiment. The processing from Step S51 to Step S54 in the modification of the fourth embodiment is the same as that of the fourth embodiment (refer to FIG. 26).

The output processor 50 determines whether the latest vascular pattern has shifted from the initial vascular pattern (Step S65). Specifically, the output processor 50 compares, as the processing at Step S65, the positional relation between the vascular pattern acquired by the processing at Step S51 and the partial detection areas PAA with the positional relation between the vascular pattern acquired by the processing at Step S54 and the partial detection areas PAA. The output processor 50 determines whether the position of the partial detection areas PAA in which the same vascular pattern was detected has shifted, based on the collation processing such as the detection of the feature points included in the vascular pattern.

If the processing at Step S65 determines that the shift has occurred (Yes at Step S46), the output processor 50 sequentially performs the processing at Step S3, the processing at Step S4, and the processing at Step S15. If, in contrast, the processing at Step S65 determines that the shift has not occurred (No at Step S46), the output processor 50 performs the processing at Step S47.

As described above, the modification of the fourth embodiment is the same as the fourth embodiment except in the respects otherwise explained.

In the above description, the method has been described for repeatedly acquiring the outputs from all the optical sensors (photodiodes PD) during the predetermined period Pt. However, the operation control of the optical sensors is not limited thereto. The detection controller 11 may generate the full operation period for operating all the optical sensors (photodiodes PD) at a cycle of a predetermined period, and may operate, during a period other than the full operation period, some of the optical sensors including the optical sensor that has produced the largest output during the full operation period or that has produced the output having the largest degree of variation during the full operation period. In this case, as indicated by a dashed line in FIG. 2, the output processor 50 feeds information back to detection controller 11, which indicates the position of an optical sensor that has produced the largest output during the full operation period or that has produced the output having the largest degree of variation during the full operation period, or indicates the group area PAG including the optical sensor. Based on the information fed back from the output processor 50, the detection controller 11 identifies and operates some of the optical sensors including the optical sensor that has produced the largest output during the full operation period or that has produced the output having the largest degree of variation during the full operation period.

For example, a full operation period Ba is set within the predetermined period Pt from the first timing Ta to the second timing Tb in FIG. 16, the full operation period Ba being a period in which all the partial detection areas PAA are operated. The detection signal Vdet having the largest degree of variation during the full operation period Ba is identified; and the partial detection area PAA provided in an area where the partial detection area PAA provided in a group area PAG including the partial detection area PAA that has output the identified detection signal Vdet is included, or the group area PAG is included, and where not all the partial detection areas PAA are included, is determined as the partial detection area PAA that operates during a period Aa other than the full operation period. The detection signal Vdet having the largest degree of variation during the full operation period Ba and the period Aa is identified, and data based on the output from the group area PAG including the partial detection area PAA that has output the identified detection signal Vdet having the largest degree of variation is output as the pulse wave data. The pulse wave data based on the output from the group area PAG including the partial detection area PAA that has output the detection signal Vdet having the largest degree of variation refers to, for example, the pulse wave data obtained through the averaging processing. The relation between a full operation period Bb and a period Ab set in the predetermined period Pt from the second timing Tb to the third timing Tc is the same as that in the operation control in the full operation period Ba and the period Aa. The relation between a full operation period Bc and a period Ac set in the predetermined period Pt from the third timing Tc to the fourth timing Td is also the same as that in the operation control in the full operation period Ba and the period Aa. The operation control in the full operation period and the period other than the full operation period set in the predetermined period Pt thereafter is the same as the operation control in the full operation period Ba and the period Aa.

The area where the group area PAG including the partial detection area PAA that has output the detection signal Vdet having the largest degree of variation during the full operation period (for example, the full operation period Ba, Bb, or Bc) is included and where not all the partial detection areas PAA are included, refers to an area including a plurality of group areas PAG located in the same position in the first direction Dx or the second direction Dy as in the group area PAG, for example. The area is, however, not limited thereto and may be changed as appropriate.

As described above, the detection controller 11 for controlling the operation of the optical sensors (for example, the photodiodes PD) generates the full operation period (for example, the full operation period Ba, Bb, or Bc) in which all the optical sensors are operated at the cycle of the predetermined period (for example, the predetermined period Pt). During the period (for example, the period Aa, Ab, or Ac) other than the full operation period, the detection controller 11 operates some of the optical sensors including the optical sensor that has produced the largest output during the full operation period or that has produced the output having the largest degree of variation during the full operation period. This configuration can reduce the number of the optical sensors that operate during the period other than the full operation period. Thus, the refresh rate of the optical sensors operated during the period other than the full operation period can be increased more easily.

The detection signals Vdet to be averaged are not limited to the detection signals Vdet from the partial detection areas PAA provided in one of the group areas PAG. For example, the detection signal Vdet of one partial detection area PAA that has output the detection signal Vdet having the largest degree of variation and the detection signal Vdet of another partial detection area PAA having a positional relation satisfying a predetermined condition with the one partial detection area PAA may be averaged. Examples of the predetermined condition include a condition that at least one of the position in the first direction Dx and the position in the second direction Dy of the partial detection area PAA is the same as the position of the one partial detection area PAA that has output the detection signal Vdet having the largest degree of variation, a condition that the number of other partial detection areas PAA interposed between the one partial detection areas PAA and the other partial detection areas PAA is within a predetermined number, and a condition that a combination of these conditions is satisfied. The value of the predetermined number is preferably sufficiently smaller than the number of the partial detection areas PAA arranged in the first direction Dx and the number of the partial detection areas PAA arranged in the second direction Dy.

The averaging processing is not essential. For example, for the group area PAG including the partial detection area PAA that has output the detection signal Vdet having the largest degree of variation during the full operation period (for example, the full operation period Ba, Bb, or Bc), at least either the gate lines GCL or the signal lines SGL in the group area PAG may be collectively driven during the period (for example, the period Aa, Ab, or Ac) other than the full operation period, and the detection signals Vdet from the partial detection areas PAA provided in the group area PAG may be integrated.

The size and characteristics of the partial detection areas PAA need not be uniform. For example, a plurality of types of the photodiodes PD having different sensitivity may be alternately arranged to increase the dynamic range of the entire partial detection areas PAA.

Figure 28:
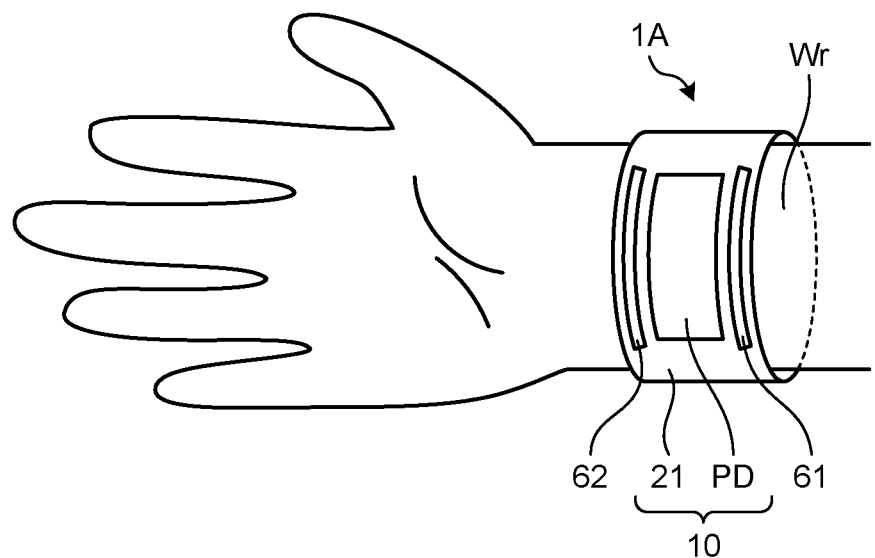
FIG. 28 is a schematic view illustrating a main configuration example of a detection device in a form wearable on a wrist.
Figure 29:
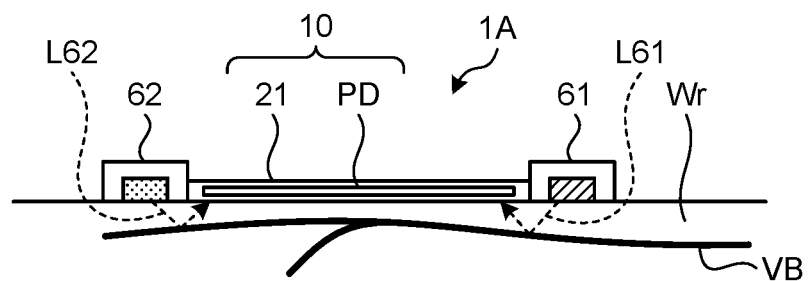
FIG. 29 is a schematic view illustrating an example of detection of the blood vessel by the detection device illustrated in FIG. 28.

The specific form of the detection device 1 is not limited to the form described with reference to FIGS. 11 to 13. FIG. 28 is a schematic view illustrating a main configuration example of a detection device 1A in a form wearable on the wrist Wr. FIG. 29 is a schematic diagram illustrating an example of the detection of the blood vessel VB by the detection device 1A illustrated in FIG. 28. As illustrated in FIG. 28, the sensor base member 21 of the detection device 1A has flexibility to be deformable into an annular shape surrounding the wrist Wr. The photodiodes PD, the first light sources 61, and the second light sources 62 are arranged in an arc shape along the annular sensor base member 21.

Figure 30:
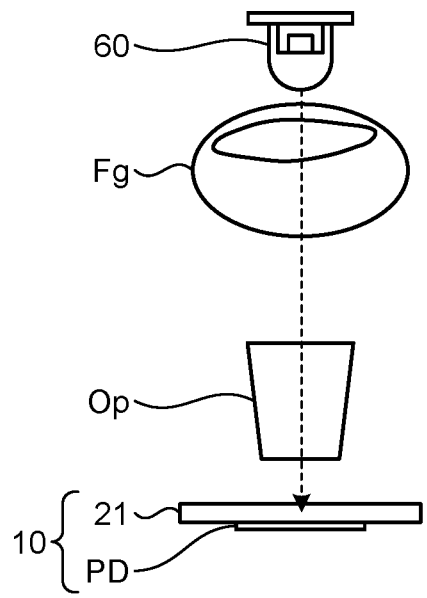
FIG. 30 is a diagram illustrating a configuration example in which a lens is provided between the finger and the sensor.

The sensor 10 need not directly contact the living body tissue. FIG. 30 is a configuration example in which a lens Op is provided between the finger Fg and the sensor 10. As illustrated in FIG. 30, the lens Op may be provided in a position that faces a light source 60 with the living body tissue (for example, the finger Fg) interposed therebetween, and is interposed between the living body tissue and the sensor 10. The light source 60 includes at least either the first light sources 61 or the second light sources 62. The lens Op is, for example, an optical lens that condenses light traveling from the light source 60 toward the sensor 10.

The detection device 1 and the detection device 1A may be further provided with a component, serving as a different sensor from the photodiode PD, capable of detecting, for example, the fingerprint using the capacitance method.

Figure 31:
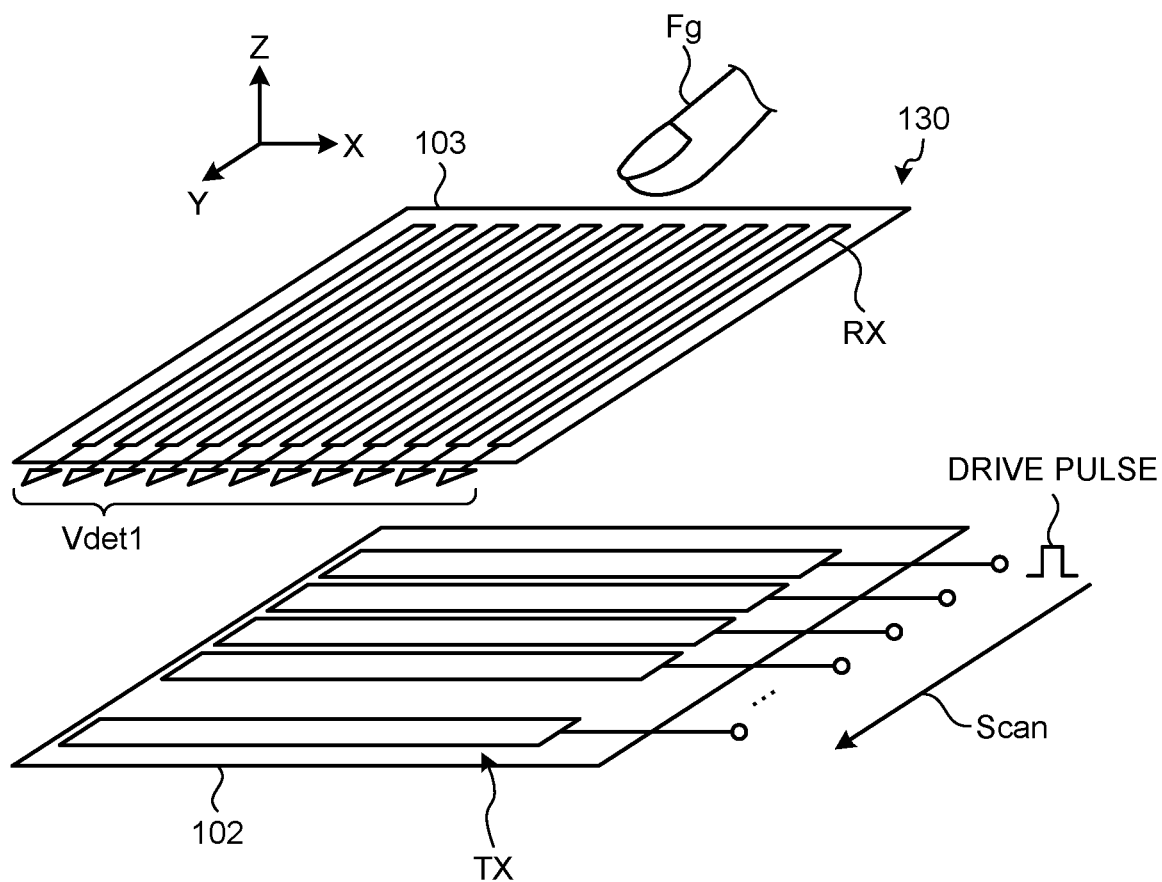
FIG. 31 is a schematic diagram illustrating a main configuration example of a mutual capacitive sensor.

FIG. 31 is a schematic diagram illustrating a main configuration example of a mutual capacitive sensor 130. The sensor 130 includes a first substrate 102 and a second substrate 103 arranged so as to face each other. The first substrate 102 and the second substrate 103 extend along a plane (XY plane) orthogonal to the facing direction (Z-direction). The XY plane need not be a fixed immovable plane. The first direction Dx-second direction Dy plane is allowed to be displaced as well as being allowed to be, for example, curved depending on the flexibility of the sensor base member 21. In the following description, for ease of understanding, "X-direction" and "Y-direction" denote two directions along the plane (XY plane) orthogonal to the Z-direction of FIG. 31. The X-direction is orthogonal to the Y-direction.

The first substrate 102 is provided with a plurality of first electrodes TX that have a longitudinal direction along the X-direction and are arranged along the Y-direction. The second substrate 103 is provided with a plurality of second electrodes Rx that have a longitudinal direction along the Y-direction and are arranged along the X-direction. The first electrodes TX face the second electrodes Rx in the Z-direction in a non-contact state. The sensor 130 is provided so as to come into proximity to or contact with an external object such as the finger Fg on the second substrate 103 side.

When scanning Scan is performed to sequentially apply drive pulses to the first electrodes TX, capacitance is generated between the second electrodes Rx and the first electrodes TX to which the drive pulses are applied. If, for example, the finger Fg comes into proximity to or contact with the second electrodes Rx, the capacitance varies. For example, the fingerprint or the like can be detected by acquiring the presence or absence of variation in the capacitance and the degree of the variation in the capacitance, as a detection signal Vdet1 from the second electrodes Rx.

The position of the sensor 130 is associated with the position of the sensor 10 in advance. While the sensor 130 is disposed in, for example, the detection device 1 so as to face the finger Fg with, for example, the sensor 10 interposed therebetween, the arrangement is not limited thereto. For example, the first electrodes TX and the second electrodes Rx may be transparent electrodes of, for example, indium tin oxide (ITO), and may be arranged on the finger Fg side from the sensor 10. The first electrodes TX and the second electrodes Rx may be individually driven to serve as a self-capacitive sensor.

Figure 32:
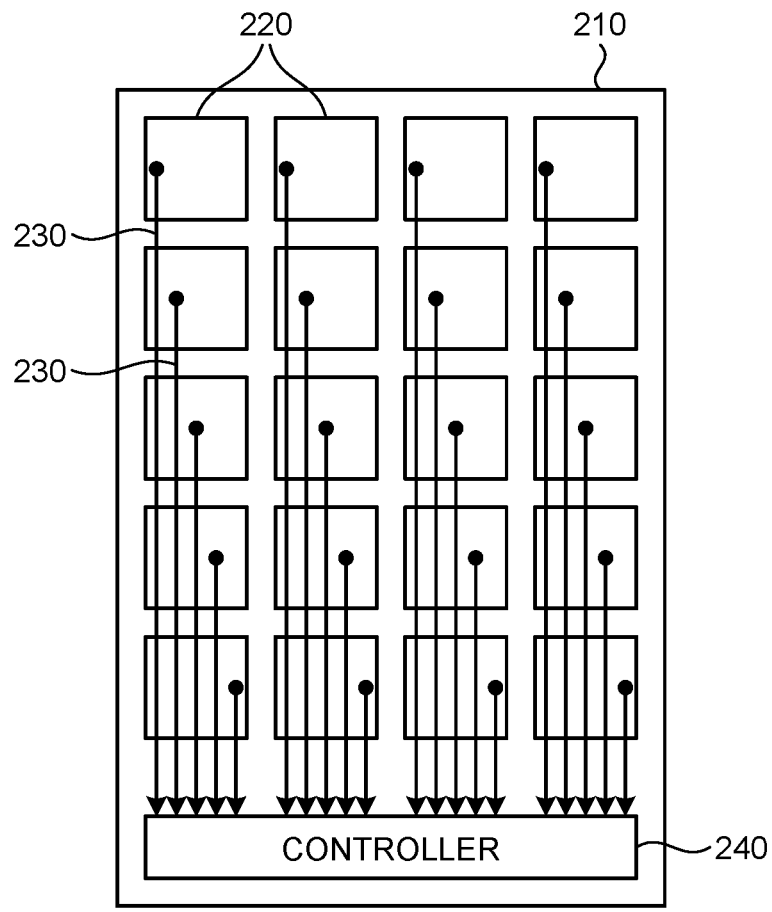
FIG. 32 is a schematic diagram illustrating a main configuration example of a self-capacitive sensor.

FIG. 32 is a schematic diagram illustrating a main configuration example of a self-capacitive sensor 210. The sensor 210 includes a plurality of electrodes 220. The electrodes 220 are arranged, for example, in a matrix having a row-column configuration. The self-capacitance held in each of the electrodes 220 varies when, for example, the finger Fg comes into proximity to or contact with the electrode 220. A controller 240 coupled to the electrodes 220 through wiring 230 is a circuit that detects the presence or absence of variation in the self-capacitance and the degree of the variation in the self-capacitance.

The position of the sensor 210 is associated with the position of the sensor 10 in advance. While the sensor 210 is disposed in, for example, the detection device 1 so as to face the finger Fg with, for example, the sensor 10 interposed therebetween, the arrangement is not limited thereto. For example, the electrodes 220 may be transparent electrodes of, for example, indium tin oxide (ITO), and may be arranged on the finger Fg side from the sensor 10.

The detection device 1 can be mounted on various products supposed to be in contact with or in proximity to the living body tissue. Mounting examples of the detection device 1 will be described with reference to FIGS. 33, 34, and 35.

Figure 33:
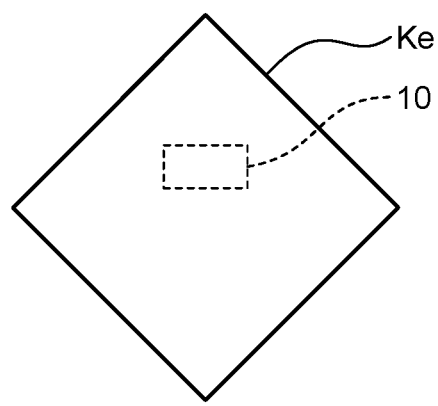
FIG. 33 is a diagram illustrating an arrangement example of the sensor of the detection device mounted on a bandanna.
Figure 34:
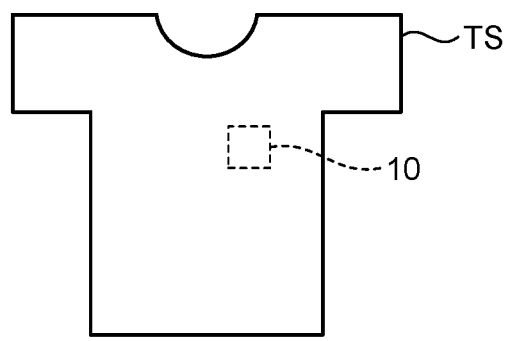
FIG. 34 is a diagram illustrating an arrangement example of the sensor of the detection device mounted on clothes.
Figure 35:
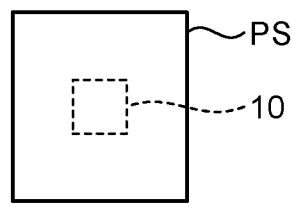
FIG. 35 is a diagram illustrating an arrangement example of the sensor of the detection device mounted on an adhesive sheet.

FIG. 33 is a diagram illustrating an arrangement example of the sensor 10 of the detection device 1 mounted on a bandanna Ke. FIG. 34 is a diagram illustrating an arrangement example of the sensor 10 of the detection device 1 mounted on clothes TS. FIG. 35 is a diagram illustrating an arrangement example of the sensor 10 of the detection device 1 mounted on an adhesive sheet PS. For example, the detection device 1 may be incorporated into a product, such as the bandanna Ke of FIG. 33, the clothes TS of FIG. 34, or the adhesive sheet PS of FIG. 35, that is operated to contact the living body tissue. In this case, at least the sensor 10 is preferably provided at a position expected to contact the living body tissue when the product is used. Although not illustrated, the light sources such as the first light sources 61 and the second light sources 62 are preferably arranged taking into account the positional relation between the sensor 10 and the living body tissue. The products are not limited to the bandanna Ke, the clothes TS, and the adhesive sheet PS. The detection device 1 can be incorporated into any product expected to contact the living body tissue when the product is in use. The adhesive sheet PS is a sheet-like product provided with adhesiveness, such as external analgesic and anti-inflammatory sheets.

In the embodiments, the case has been described where the gate line drive circuit 15 performs the time-division selective driving of sequentially supplying the gate drive signals Vgcl to the gate lines GCL. However, the driving method is not limited to this case. The sensor 10 may perform code division selection driving (hereinafter, called "code division multiplexing (CDM) driving") to perform the detection. Since the CDM driving and a drive circuit thereof are described in Japanese Patent Application No. 2018-005178 (JP-A-2018-005178), what is described in JP-A-2018-005178 is included in the embodiments and the modification (the embodiments or the like), and the description will not be omitted herein.

The gate lines GCL preferably extend along a general direction of blood flow. Specifically, the gate lines GCL in the sensor 10 extending along an arc of the annular sensor base member 21 wound around the finger Fg or the wrist Wr preferably extend along the central axis of the annulus.

Although the preferred embodiments and the like of the present invention have been described above, the present invention is not limited to the embodiments or the like described above. The content disclosed in the embodiments or the like is merely an example, and can be variously modified within the scope not departing from the gist of the present invention. Any modifications appropriately made within the scope not departing from the gist of the present invention also naturally belong to the technical scope of the present invention.

What is claimed is:

1. A detection device comprising:
    a plurality of optical sensors arranged in a detection area that is divided into a plurality of group areas; and
    a detection circuit configured to determine an optical sensor to be employed from among the optical sensors in the group areas based on outputs of the respective optical sensors,
    wherein each of the group areas comprises the optical sensors each disposed in a partial detection area, and
    wherein the detection circuit is configured to employ an output of the group area including the partial detection area in which the optical sensor that has produced an output having a largest degree of variation during a predetermined period.

2. The detection device according to claim 1,
    wherein the detection circuit is configured to
    generate a full operation period for operating all the optical sensors at the cycle of the predetermined period, and
    operate, during a period other than the full operation period, some of the optical sensors including the optical sensor that has produced the output having the largest degree of variation during the full operation period.

3. The detection device according to claim 1,
    wherein the optical sensors are arranged in a plurality of partial detection areas on a one-to-one basis, the partial detection areas being arranged in a matrix having a row-column configuration in the detection area, and
    wherein the detection circuit is configured to
    perform averaging processing to average outputs of a predetermined number of the optical sensors that are two or more adjacent optical sensors in adjacent partial detection areas and that are not all the optical sensors, and
    determine, based on an output averaged by the averaging processing, the optical sensor producing an output to be employed.

4. The detection device according to claim 3,
    wherein the predetermined number of the optical sensors are arranged along at least one direction in the detection area.

5. The detection device according to claim 1,
    wherein the detection area is configured to face a finger, and
    wherein the detection circuit is configured to determine, based on a fingerprint pattern generated based on the outputs of the respective optical sensors, the optical sensor producing an output to be employed, among the optical sensors.

6. The detection device according to claim 1,
    wherein the detection area is configured to face a living body tissue including a blood vessel in the living body tissue, and
    wherein the detection circuit is configured to determine, based on a vascular pattern generated based on the outputs of the respective optical sensors, the optical sensor producing an output to be employed, among the optical sensors.

7. The detection device according to claim 1,
    wherein the detection circuit is configured to detect a pulse wave based on an output of the optical sensor employed from among the optical sensors.

8. The detection device according to claim 1, further comprising a light source configured to emit light that is emitted to an object to be detected and is detected by the optical sensors.

9. The detection device according to claim 8,
    wherein the light source emits a blue light or a green light.

10. The detection device according to claim 8,
    wherein the light source emits an infrared light.

* * * * *